(12) United States Patent
Goldberg

(10) Patent No.: US 6,437,112 B1
(45) Date of Patent: Aug. 20, 2002

(54) MATERIALS FOR THE PRODUCTION OF NANOMETER STRUCTURES AND USE THEREOF

(75) Inventor: Edward B. Goldberg, Newton, MA (US)

(73) Assignee: NanoFrames, LLC, Boston, MA (US)

( * ) Notice: Subject to any disclaimer, the term of this patent is extended or adjusted under 35 U.S.C. 154(b) by 0 days.

(21) Appl. No.: 09/236,949

(22) Filed: Jan. 25, 1999

Related U.S. Application Data

(60) Division of application No. 08/542,003, filed on Oct. 12, 1995, now Pat. No. 5,864,013, which is a continuation-in-part of application No. 08/322,760, filed on Oct. 13, 1994, now Pat. No. 5,877,279.

(51) Int. Cl.⁷ .............................................. C07H 21/04
(52) U.S. Cl. ..................................................... 536/23.4
(58) Field of Search .............................. 536/23.1, 23.4; 530/300, 350

(56) References Cited

U.S. PATENT DOCUMENTS

| 3,532,593 A | 10/1970 | Tang |
| 5,864,013 A | 1/1999 | Goldberg |
| 5,877,279 A | 3/1999 | Goldberg |

OTHER PUBLICATIONS

Sandmeier, 1994, Acquisition and rearrangement of sequence motifs in the evolution of bacteriophage tail fibres, Molecular Microbiology, 12(3):344–50.

Repoila et al., 1994, Genomic polymorphism in the T–even bacteriophages, EMBO J. 13(17):4181–92.

Wood et al., 1983, Long tail fibers: genes, proteins, assembly, and structure, in Bacteriophage T4, Mathews, Kutter, Mosig and Berget (eds.), American Society of Microbiology, Washington, D.C., pp. 259–269.

Monod et al., 1997, The genome of the pseudo t–even bacteriophages, a diverse group that resembles T4, J. Mol. Biol. 267: 237–49.

Tétart et al., 2001, Phylogeny of the major head and tail genes of the wide–ranging T4–type bacteriophages, Journal of Bacteriology 183(1):358–66.

Hahn et al., 1989, Organization of the bacteriophage T4 genome between map positions 150.745 and 145.824, Nucleic Acids Res. 17:6729.

Robertson et al., 1991, Use of group–specific primers and the polymerase chain reaction for the detection and identification of luteoviruses, J. Gen. Virol. 72:1473–77.

Langeveld et al., 1991, Identification of potyviruses using the polymerase chain reaction with degenerate primers, J. Gen. Virol. 72:1531–41.

Montag et al., 1987, Receptor–recognizing proteins of T–even type bacteriophages. Constant and hypervariable regions and an unusual case of evolution, J. Mol. Biol. 196 (1), 165–74.

Montag et al., 1990, Receptor–recognizing proteins of T–even type bacteriophages. The receptor–recognizing area of proteins 37 of phages T4 Tula and Tulb, J. Mol. Biol. 216 (2), 327–34.

Riede et al., 1984 DNA sequence heterogeneity in the genes of T–even type *Escherichia coli* phages encoding the receptor recognizing protein of the long tail, Mol. Gen. Genet. 195 (1–2), 144–52.

Snyder and Wood, Jul. 1989, Genetic Definition of Two Functional Elements in a Bacteriophage T4 Host–Range "Cassette", Genetics 122, 471–479.

Ackermann and Krisch, 1997, "A Catalogue of T–4 Type Bacteriophages", Arch. Virol. 142:2329–2345.

Beckendorf et al., 1973, "Structure of Bacteriophage T4 Genes 37 and 38", J. Mol. Biol. 73:17–35.

Beckendorf, 1973, "Structure of the Distal Half of the Bacteriophage T4 Tail Fiber", J. Mol. Biol. 73:37–53.

Haggård–Ljungquist et al., 1992, "DNA Sequences of the Tail Fiber Genes of Bacteriophage P2: Evidence of Horizontal Transfer for Tail Fiber Genes among Unrelated Bacteriophages", J. Bacteriol. 174:1462–1477.

Henning and Hashemolhosseini, 1994, "Receptor Recognition by T–Even–Type Coliphages", Chapter 23 in Molecular Biology of Bacteriophage T4, Karam, ed., American Society for Microbiology, Washington, D.C., pp. 291–298.

Riede et al., 1986, "DNA Sequence of the Tail Fiber Genes 37, Encoding the Receptor Recognizing Part of the Fiber, of Bacteriophages T2 and K3", J. Mol. Biol. 191:255–266.

Riede et al., 1985, "The Nucleotide Sequences of the Tail Fiber Gene 36 of Bacteriophage T2 and of Genes 36 of the T Type *Escherichia coli* Phages K3 and Ox2", Nucl. Acids Res. 13:605–616.

Russell, 1974, "Comparative Genetics of the T–Even Bacteriophages", Genetics 78:967–988.

Bella et al., 1994, "Crystal and molecular structure of a collagen–like peptide at 1.9Å resolution", Science 226:75–81.

T.E. Creighton (ed.), 1984, *Proteins, Structures and Molecular Principles*, W.H. Freeman & Co, NY, pp. 25–28.

Earnshaw et al., 1979, "The distal half of the tail fibre of the bacteriophage T4 rigidly linked domains and cross–β structure", J Mol Biol 132:101–131.

(List continued on next page.)

*Primary Examiner*—Karen Cochrane Carlson
(74) *Attorney, Agent, or Firm*—Pennie & Edmonds LLP

(57) ABSTRACT

The present invention pertains to nanostructures, i.e., nanometer sized structures useful in the construction of microscopic and macroscopic structures. In particular, the present invention pertains to nanostructures based on bacteriophage T4 tail fiber proteins and variants thereof.

13 Claims, 26 Drawing Sheets

OTHER PUBLICATIONS

Edgar and Lielausis, 1965, "Serological studies with mutants of phage T4D defective in genes determining tail fiber structure", Genetics 52:1187–1200.

Freedman, 1991, "Exploiting the nanotechnology of life", Science 254(29):1308–1310.

Harbury et al., 1993, "A switch between two–, and four–-stranded coiled coils in GCN4 Leucine zipper mutants", Science 262:1401–1407.

Henning et al., 1994, "Receptor recognition by T–even–type coliphages", in Molecular Biology of Bacteriophage T4, Karam (ed.), American Society of Microbiology, Washington D.C. pp. 291–298.

Hutchison III, et al., Meth Enzymol 202:356–391.

Levy et al., 1980, "Region–specific recombination in phage T4. II. Structure of the recombinants", Genetics 94:531–547.

O'Shea et al., 1989, "Evidence that the leucine zipper is a coiled coil", Science 243:538–542.

Oliver and Crowther, 1981, "DNA Sequence of the tail fibre genes 36 and 37 of bacteriophage T4", J Mol Biol 153:545–568.

S.P. Parker (ed), 1994, *Concise Encyclopedia of Science & Technolgy*, McGraw Hill Inc, NY, p. 1354.

Seed, 1980, "Studies of the bacteriophage T4 proximal half tail fiber", Ph.D. Thesis (C.I.T.).

Steven et al., 1988, "Molecular substructure of a viral receptor–recoginition protein: The gp17 tail fiber of bacteriophage T7", J Mol Biol 200:351–365.

Ward et al., 1970, "Assembly of bacteriophage T4 tail fibers II. Isolation and characterization of tail fiber precursors", J Mol Biol 54:15–31.

Whitesides et al., 1991, "Molecular self–assembly and nanochemistry: A chemical strategy for the synthesis of nanostructures", Science 254(29):1312–1318.

Wood et al., 1994, "Long tail fibers: Genes, proteins, structure and assembly", in Molecular Biology of Bacteriophage T4, Karam (ed.), American Society of Microbiology, Washington, D.C. pp. 282–290.

```
        |   10       |   20       |   30       |   40       |   50       |   60
   1    TAGGAGCCCG   GGAGAATGGC   CGAGATTAAA   AGAGAATTCA   GAGCAGAAGA   TGGTCTGGAC    60
  61    GCAGGTGGTG   ATAAAATAAT   CAACGTAGCT   TTAGCTGATC   GTACCGTAGG   AACTGACGGT   120
 121    GTTAACGTTG   ATTACTTAAT   TCAAGAAAAC   ACAGTTCAAC   AGTATGATCC   AACTCGTGGA   180
 181    TATTTAAAAG   ATTTTGTAAT   CATTTATGAT   AACCGCTTTT   GGGCTGCTAT   AAATGATATT   240
 241    CCAAAACCAG   CAGGAGCTTT   TAATAGCGGA   CGCTGGAGAG   CATTACGTAC   CGATGCTAAC   300
 301    TGGATTACGG   TTTCATCTGG   TTCATATCAA   TTAAAATCTG   GTGAAGCAAT   TTCGGTTAAC   360
 361    ACCGCAGCTG   GAAATGACAT   CACGTTTACT   TTACCATCTT   CTCCAATTGA   TGGTGATACT   420
 421    ATCGTTCTCC   AAGATATTGG   AGGAAAACCT   GGAGTTAACC   AAGTTTTAAT   TGTAGCTCCA   480
 481    GTACAAAGTA   TTGTAAACTT   TAGAGGTGAA   CAGGTACGTT   CAGTACTAAT   GACTCATCCA   540
 541    AAGTCACAGC   TAGTTTTAAT   TTTTAGTAAT   CGTCTGTGGC   AAATGTATGT   TGCTGATTAT   600
 601    AGTAGAGAAG   CTATAGTTGT   AACACCAGCG   AATACTTATC   AAGCGCAATC   CAACGATTTT   660
 661    ATCGTACGTA   GATTTACTTC   TGCTGCACCA   ATTAATGTCA   AACTTCCAAG   ATTTGCTAAT   720
 721    CATGGCGATA   TTATTAATTT   CGTCGATTTA   GATAAACTAA   ATCCGCTTTA   TCATACAATT   780
 781    GTTACTACAT   ACGATGAAAC   GACTTCAGTA   CAAGAAGTTG   GAACTCATTC   CATTGAAGGC   840
 841    CGTACATCGA   TTGACGGTTT   CTTGATGTTT   GATGATAATG   AGAAATTATG   GAGACTGTTT   900
 901    GACGGGGATA   GTAAAGCGCG   TTTACGTATC   ATAACGACTA   ATTCAAACAT   TCGTCCAAAT   960
 961    GAAGAAGTTA   TGGTATTTGG   TGCGAATAAC   GGAACAACTC   AAACAATTGA   GCTTAAGCTT   1020
1021    CCAACTAATA   TTTCTGTTGG   TGATACTGTT   AAAATTTCCA   TGAATTACAT   GAGAAAAGGA   1080
1081    CAAACAGTTA   AAATCAAAGC   TGCTGATGAA   GATAAAATTG   CTTCTTCAGT   TCAATTGCTG   1140
1141    CAATTCCCAA   AACGCTCAGA   ATATCCACCT   GAAGCTGAAT   GGGTTACAGT   TCAAGAATTA   1200
1201    GTTTTTAACG   ATGAAACTAA   TTATGTTCCA   GTTTTGGAGC   TTGCTTACAT   AGAAGATTCT   1260
1261    GATGGAAAAT   ATTGGGTTGT   ACAGCAAAAC   GTTCCAACTG   TAGAAAGAGT   AGATTCTTTA   1320
1321    AATGATTCTA   CTAGAGCAAG   ATTAGGCGTA   ATTGCTTTAG   CTACACAAGC   TCAAGCTAAT   1380
1381    GTCGATTTAG   AAAATTCTCC   ACAAAAAGAA   TTAGCAATTA   CTCCAGAAAC   GTTAGCTAAT   1440
1441    CGTACTGCTA   CAGAAACTCG   CAGAGGTATT   GCAAGAATAG   CAACTACTGC   TCAAGTGAAT   1500
1501    CAGAACACCA   CATTCTCTTT   TGCTGATGAT   ATTATCATCA   CTCCTAAAAA   GCTGAATGAA   1560
1561    AGAACTGCTA   CAGAAACTCG   TAGAGGTGTC   GCAGAAATTG   CTACGCAGCA   AGAAACTAAT   1620
1621    GCAGGAACCG   ATGATACTAC   AATCATCACT   CCTAAAAAGC   TTCAAGCTCG   TCAAGGTTCT   1680
1681    GAATCATTAT   CTGGTATTGT   AACCTTTGTA   TCTACTGCAG   GTGCTACTCC   AGCTTCTAGC   1740
1741    CGTGAATTAA   ATGGTACGAA   TGTTTATAAT   AAAAACACTG   ATAATTTAGT   TGTTTCACCT   1800
1801    AAAGCTTTGG   ATCAGTATAA   AGCTACTCCA   ACACAGCAAG   GTGCAGTAAT   TTTAGCAGTT   1860
1861    GAAAGTGAAG   TAATTGCTGG   ACAAAGTCAG   CAAGGATGGG   CAAATGCTGT   TGTAACGCCA   1920
1921    GAAACGTTAC   ATAAAAAGAC   ATCAACTGAT   GGAAGAATTG   GTTTAATTGA   AATTGCTACG   1980
1981    CAAAGTGAAG   TTAATACAGG   AACTGATTAT   ACTCGTGCAG   TCACTCCTAA   AACTTTAAAT   2040
2041    GACCGTAGAG   CAACTGAAAG   TTTAAGTGGT   ATAGCTGAAA   TTGCTACACA   AGTTGAATTC   2100
2101    GACGCAGGCG   TCGACGATAC   TCGTATCTCT   ACACCATTAA   AAATTAAAAC   CAGATTTAAT   2160
2161    AGTACTGATC   GTACTTCTGT   TGTTGCTCTA   TCTGGATTAC   TTGAATCAGG   AACTCTCTGG   2220
2221    GACCATTATA   CACTTAATAT   TCTTGAAGCA   AATGAGACAC   AACGTGGTAC   ACTTCGTGTA   2280
2281    GCTACGCAGG   TCGAAGCTGC   TGCGGGAACA   TTAGATAATG   TTTTAATAAC   TCCTAAAAAG   2340
```

FIG.6A

```
2341   CTTTTAGGTA CTAAATCTAC TGAAGCGCAA GAGGGTGTTA TTAAAGTTGC AACTCAGTCT 2400
2401   GAAACTGTGA CTGGAACGTC AGCAAATACT GCTGTATCTC CAAAAAATTT AAAATGGATT 2460
2461   GCGCAGAGTG AACCTACTTG GGCAGCTACT ACTGCAATAA GAGGTTTTGT TAAAACTTCA 2520
2521   TCTGGTTCAA TTACATTCGT TGGTAATGAT ACAGTCGGTT CTACCCAAGA TTTAGAACTG 2580
2581   TATGAGAAAA ATAGCTATGC GGTATCACCA TATGAATTAA ACCGTGTATT AGCAAATTAT 2640
2641   TTGCCACTAA AAGCAAAAGC TGCTGATACA AATTTATTGG ATGGTCTAGA TTCATCTCAG 2700
2701   TTCATTCGTA GGGATATTGC ACAGACGGTT AATGGTTCAC TAACCTTAAC CCAACAAACG 2760
2761   AATCTGAGTG CCCCTCTTGT ATCATCTAGT ACTGGTGAAT TGGTGGTTC ATTGGCCGCT 2820
2821   AATAGAACAT TTACCATCCG TAATACAGGA GCCCCGACTA GTATCGTTTT CGAAAAACGT 2880
2881   CCTGCATCCG GGCAAATCC TGCACAGTCA ATGAGTATTC GTCTATGGGG TAACCAATTT 2940
2941   GGCGGCGGTA GTGATACGAC CCGTTCGACA GTGTTTGAAG TTGGCGATGA CACATCTCAT 3000
3001   CACTTTTATT CTCAACGTAA TAAAGACGGT AATATAGCGT TAACATTAA TGGTACTGTA 3060
3061   ATGCCAATAA ACATTAATGC TTCCGGTTTG ATGAATGTGA ATGGCACTGC AACATTCGGT 3120
3121   CGTTCAGTTA CAGCCAATGG TGAATTCATC AGCAAGTCTG CAAATGCTTT TAGAGCAATA 3180
3181   AACGGTGATT ACGGATTCTT TATTCGTAAT GATGCCTCTA ATACCTATT TTTGCTCACT 3240
3241   GCAGCCGGTG ATCAGACTGG TGGTTTTAAT GGATTACGCC CATTATTAAT TAATAATCAA 3300
3301   TCCGGTCAGA TTACAATTGG TGAAGGCTTA ATCATTGCCA AAGGTGTTAC TATAAATTCA 3360
3361   GGCGGTTTAA CTGTTAACTC GAGAATTCGT TCTCAGGGTA CTAAAACATC TGATTTATAT 3420
3421   ACCCGTGCGC CAACATCTGA TACTGTAGGA TTCTGGTCAA TCGATATTAA TGATTCAGCC 3480
3481   ACTTATAACC AGTTCCCGGG TTATTTTAAA ATGGTTGAAA AAACTAATGA ACTGACTGGG 3540
3541   CTTCCATACT TAGAACGTGG CGAAGAAGTT AAATCTCCTG GTACACTGAC TCAGTTTGGT 3600
3601   AACACACTTG ATTCGCTTTA CCAAGATTCG ATTACTTATC AACGACGCC AGAAGCGCGT 3660
3661   ACCACTCGCT GGACACGTAC ATGGCAGAAA ACCAAAAACT CTTGGTCAAG TTTTGTTCAG 3720
3721   GTATTTGACG GAGGTAACCC TCCTCAACCA TCTGATATCG GTGCTTTACC ATCTGATAAT 3780
3781   GCTACAATGG GGAATCTTAC TATTCGTGAT TTCTTGCGAA TTGGTAATGT TCGCATTGTT 3840
3841   CCTGACCCAG TGAATAAAAC GGTTAAATTT GAATGGGTTG AATAAGAGGT ATTATGGAAA 3900
3901   AATTTATGGC CGAGATTTGG ACAAGGATAT GTCCAAACGC CATTTTATCG GAAAGTAATT 3960
3961   CAGTAAGATA TAAAATAAGT ATAGCGGGTT CTTGCCCGCT TTCTACAGCA GGACCATCAT 4020
4021   ATGTTAAATT TCAGGATAAT CCTGTAGGAA GTCAAACATT TAGGCGCAGG CCTTCATTTA 4080
4081   AGAGTTTTTG ACCCTTCCAC CGGAGCATTA GTTGATAGTA AGTCATATGC TTTTTCGACT 4140
4141   TCAAATGATA CTACATCAGC TGCTTTTGTT AGTTTTCATG AATTCTTTGA CGAATAATCG 4200
4201   AATTGTTGCT ATATTAACTA GTGGAAAGGT TAATTTTCCT CCTGAAGTAG TATCTTGGTT 4260
4261   AAGAACCGCC GGAACGTCTG CCTTTCCATC TGATTCTATA TTGTCAAGAT TTGACGTATC 4320
4321   ATATGCTGCT TTTTATACTT CTTCTAAAAG AGCTATCGCA TTAGAGCATG TTAAACTGAG 4380
4381   TAATAGAAAA AGCACAGATG ATTATCAAAC TATTTTAGAT GTTGTATTTG ACAGTTTAGA 4440
4441   AGATGTAGGA GCTACCGGGT TTCCAAGAAG AACGTATGAA AGTGTTGAGC AATTCATGTC 4500
4501   GGCAGTTGGT GGAACTAATA ACGAAATTGC GAGATTGCCA ACTTCAGCTG CTATAAGTAA 4560
4561   ATTATCTGAT TATAATTTAA TTCCTGGAGA TGTTCTTTAT CTTAAAGCTC AGTTATATGC 4620
4621   TGATGCTGAT TTACTTGCTC TTGGAACTAC AAATATATCT ATCCGTTTTT ATAATGCATC 4680
4681   TAACGGATAT ATTTCTTCAA CACAAGCTGA ATTTACTGGG CAAGCTGGGT CATGGGAATT 4740
```

FIG.6B

```
4741  AAAGGAAGAT TATGTAGTTG TTCCAGAAAA CGCAGTAGGA TTTACGATAT ACGCACAGAG  4800
4801  AACTGCACAA GCTGGCCAAG GTGGCATGAG AAATTTAAGC TTTTCTGAAG TATCAAGAAA  4860
4861  TGGCGGCATT TCGAAACCTG CTGAATTTGG CGTCAATGGT ATTCGTGTTA ATTATATCTG  4920
4921  CGAATCCGCT TCACCTCCGG ATATAATGGT ACTTCCTACG CAAGCATCGT CTAAAACTGG  4980
4981  TAAAGTGTTT GGGCAAGAAT TTAGAGAAGT TTAAATTGAG GGACCCTTCG GGTTCCCTTT  5040
5041  TTCTTTATAA ATACTATTCA AATAAAGGGG CATACAATGG CTGATTTAAA AGTAGGTTCA  5100
5101  ACAACTGGAG GCTCTGTCAT TTGGCATCAA GGAAATTTTC CATTGAATCC AGCCGGTGAC  5160
5161  GATGTACTCT ATAAATCATT TAAAATATAT TCAGAATATA ACAAACCACA AGCTGCTGAT  5220
5221  AACGATTTCG TTTCTAAAGC TAATGGTGGT ACTTATGCAT CAAAGGTAAC ATTTAACGCT  5280
5281  GGCATTCAAG TCCCATATGC TCCAAACATC ATGAGCCCAT GCGGGATTTA TGGGGGTAAC  5340
5341  GGTGATGGTG CTACTTTTGA TAAAGCAAAT ATCGATATTG TTTCATGGTA TGGCGTAGGA  5400
5401  TTTAAATCGT CATTTGGTTC AACAGGCCGA ACTGTTGTAA TTAATACACG CAATGGTGAT  5460
5461  ATTAACACAA AAGGTGTTGT GTCGGCAGCT GGTCAAGTAA GAAGTGGTGC GGCTGCTCCT  5520
5521  ATAGCAGCGA ATGACCTTAC TAGAAAGGAC TATGTTGATG GAGCAATAAA TACTGTTACT  5580
5581  GCAAATGCAA ACTCTAGGGT GCTACGGTCT GGTGACACCA TGACAGGTAA TTTAACAGCG  5640
5641  CCAAACTTTT TCTCGCAGAA TCCTGCATCT CAACCCTCAC ACGTTCCACG ATTGACCAA   5700
5701  ATCGTAATTA AGGATTCTGT TCAAGATTTC GGCTATTATT AAGAGGACTT ATGGCTACTT  5760
5761  TAAAACAAAT ACAATTTAAA AGAAGCAAAA TCGCAGGAAC ACGTCCTGCT GCTTCAGTAT  5820
5821  TAGCCGAAGG TGAATTGGCT ATAAACTTAA AAGATAGAAC AATTTTTACT AAAGATGATT  5880
5881  CAGGAAATAT CATCGATCTA GGTTTTGCTA AAGGCGGGCA AGTTGATGGC AACGTTACTA  5940
5941  TTAACGGACT TTTGAGATTA AATGGCCGATT ATGTACAAAC AGGTGGAATG ACTGTAAACG  6000
6001  GACCCATTGG TTCTACTGAT GGCGTCACTG GAAAAATTTT CAGATCTACA CAGGGTTCAT  6060
6061  TTTATGCAAG AGCAACAAAC GATACTTCAA ATGCCCATTT ATGGTTGAA AATGCCGATG   6120
6121  GCACTGAACG TGGCGTTATA TATGCTCGCC CTCAAACTAC AACTGACGGT GAAATACGCC  6180
6181  TTAGGGTTAG ACAAGGAACA GGAAGCACTG CCAACAGTGA ATTCTATTTC CGCTCTATAA  6240
6241  ATGGAGGCGA ATTTCAGGCT AACCGTATTT TAGCATCAGA TTCGTTAGTA ACAAAACGCA  6300
6301  TTGCGGTTGA TACCGTTATT CATGATGCCA AAGCATTTGG ACAATATGAT TCTCACTCTT  6360
6361  TGGTTAATTA TGTTTATCCT GGAACCGGTG AAACAAATGG TGTAAACTAT CTTCGTAAAG  6420
6421  TTCGCGCTAA GTCCGGTGGT ACAATTTATC ATGAAATTGT TACTGCACAA ACAGGCCTGG  6480
6481  CTGATGAAGT TTCTTGGTGG TCTGGTGATA CACCAGTATT TAAACTATAC GGTATTCGTG  6540
6541  ACGATGGCAG AATGATTATC CGTAATAGCC TTGCATTAGG TACATTCACT ACAAATTTCC  6600
6601  CGTCTAGTGA TTATGGCAAC GTCGGTGTAA TGGGCGATAA GTATCTTGTT CTCGGCGACA  6660
6661  CTGTAACTGG CTTGTCATAC AAAAAAACTG GTGTATTTGA TCTAGTTGGC GGTGGATATT  6720
6721  CTGTTGCTTC TATTACTCCT GACAGTTTCC GTAGTACTCG TAAAGGTATA TTTGGTCGTT  6780
6781  CTGAGGACCA AGGCGCAACT TGGATAATGC CTGGTACAAA TGCTGCTCTC TTGTCTGTTC  6840
6841  AAACACAAGC TGATAATAAC AATGCTGGAG ACGGACAAAC CCATATCGGG TACAATGCTG  6900
6901  GCGGTAAAAT GAACCACTAT TTCCGTGGTA CAGGTCAGAT GAATATCAAT ACCCAACAAG  6960
6961  GTATGGAAAT TAACCCGGGT ATTTTGAAAT TGGTAACTGG CTCTAATAAT GTACAATTTT  7020
7021  ACGCTGACGG AACTATTTCT TCCATTCAAC CTATTAAATT AGATAACGAG ATATTTTTAA  7080
7081  CTAAATCTAA TAATACTGCG GGTCTTAAAT TTGGAGCTCC TAGCCAAGTT GATGGCACAA  7140
```

FIG.6C

```
7141  GGACTATCCA ATGGAACGGT GGTACTCGCG AAGGACAGAA TAAAAACTAT GTGATTATTA  7200
7201  AAGCATGGGG TAACTCATTT AATGCCACTG GTGATAGATC TCGCGAAACG GTTTTCCAAG  7260
7261  TATCAGATAG TCAAGGATAT TATTTTTATG CTCATCGTAA AGCTCCAACC GGCGACGAAA  7320
7321  CTATTGGACG TATTGAAGCT CAATTTGCTG GGGATGTTTA TGCTAAAGGT ATTATTGCCA  7380
7381  ACGGAAATTT TAGAGTTGTT GGGTCAAGCG CTTTAGCCGG CAATGTTACT ATGTCTAACG  7440
7441  GTTTGTTTGT CCAAGGTGGT TCTTCTATTA CTGGACAAGT TAAAATTGGC GGAACAGCAA  7500
7501  ACGCACTGAG AATTTGGAAC GCTGAATATG GTGCTATTTT CCGTCGTTCG GAAAGTAACT  7560
7561  TTTATATTAT TCCAACCAAT CAAAATGAAG GAGAAAGTGG AGACATTCAC AGCTCTTTGA  7620
7621  GACCTGTGAG AATAGGATTA AACGATGGCA TGGTTGGGTT AGGAAGAGAT TCTTTTATAG  7680
7681  TAGATCAAAA TAATGCTTTA ACTACGATAA ACAGTAACTC TCGCATTAAT GCCAACTTTA  7740
7741  GAATGCAATT GGGGCAGTCG GCATACATTG ATGCAGAATG TACTGATGCT GTTCGCCCGG  7800
7801  CGGGTGCAGG TTCATTTGCT TCCCAGAATA ATGAAGACGT CCGTGCGCCC TTCTATATGA  7860
7861  ATATTGATAG AACTGATGCT AGTGCATATG TTCCTATTTT GAAACAACGT TATGTTCAAG  7920
7921  GCAATGGCTG CTATTCATTA GGGACTTTAA TTAATAATGG TAATTTCCGA GTTCATTACC  7980
7981  ATGGCGGCGG AGATAACGGT TCTACAGGTC CACAGACTGC TGATTTTGGA TGGGAATTTA  8040
8041  TTAAAAACGG TGATTTATT TCACCTCGCG ATTTAATAGC AGGCAAAGTC AGATTTGATA  8100
8101  GAACTGGTAA TATCACTGGT GGTTCTGGTA ATTTTGCTAA CTTAAACAGT ACAATTGAAT  8160
8161  CACTTAAAAC TGATATCATG TCGAGTTACC CAATTGGTGC TCCCGATTCCT TGGCCGAGTG  8220
8221  ATTCAGTTCC TGCTGGATTT GCTTTGATGG AAGGTCAGAC CTTTGATAAG TCCGCATATC  8280
8281  CAAAGTTAGC TGTTGCATAT CCTAGCGGTG TTATTCCAGA TATGCGCGGG CAAACTATCA  8340
8341  AGGGTAAACC AAGTGGTCGT GCTGTTTTGA GCGCTGAGGC AGATGGTGTT AAGGCTCATA  8400
8401  GCCATAGTGC ATCGGCTTCA AGTACTGACT TAGGTACTAA AACCACATCA AGCTTTGACT  8460
8461  ATGGTACGAA GGGAACTAAC AGTACGGGTG GACACACTCA CTCTGGTAGT GGTTCTACTA  8520
8521  GCACAAATGG TGAGCACAGC CACTACATCG AGGCATGGAA TGGTACTGGT GTAGGTGGTA  8580
8581  ATAAGATGTC ATCATATGCC ATATCATACA GGGCGGGTGG GAGTAACACT AATGCAGCAG  8640
8641  GGAACCACAG TCACACTTTC TCTTTTGGGA CTAGCAGTGC TGGCCGACCAT TCCCACTCTG  8700
8701  TAGGTATTGG TGCTCATACC CACACGGTAG CAATTGGATC ACATGGTCAT ACTATCACTG  8760
8761  TAAATAGTAC AGGTAATACA GAAAACACGG TTAAAAACAT TGCTTTTAAC TATATCGTTC  8820
8821  GTTTAGCATA AGGAGAGGGG CTTCGGCCCT TCTAA                              8855
        |     10   |    20    |   30    |     40  |    50  |    60
```

FIG.6D

```
1    TAGGAGCCCCGGGAGA ATG GCC GAG ATT AAA AGA GAA TTC AGA GCA GAA GAT GGT CTG GAC GCA    63
1                     M   A   E   I   K   R   E   F   R   A   E   D   G   L   D   A    16

64   GGT GGT GAT AAA ATA ATC AAC GTA GCT TTA GCT GAT CCT GAT CGT ACC GTA GGA ACT GAC GGT GTT   123
17    G   G   D   K   I   I   N   V   A   L   A   D   R   T   V   G   T   D   G   V   36

124  AAC GTT GAT TAC TTA ATT CAA GAA AAC ACA GTT CAA CAG TAT GAT CCA ACT CGT GGA TAT   183
37    N   V   D   Y   L   I   Q   E   N   T   V   Q   Q   Y   D   P   T   R   G   Y   56

184  TTA AAA GAT TTT GTA ATC ATT TAT GAT AAC CGC TTT TGG GCT GCT ATA AAT GAT ATT CCA   243
57    L   K   D   F   V   I   I   Y   D   N   R   F   W   A   A   I   N   D   I   P   76

244  AAA CCA GCA GGA GCT TTT AAT AGC GGA CGC TGG AGA GCA TTA CGT ACC GAT GCT AAC TGG   303
77    K   P   A   G   A   F   N   S   G   R   W   R   A   L   R   T   D   A   N   W   96

304  ATT ACG GTT TCA TCT GGT AAT GAC ATC ACG TTT ACT TTA CCA TCT TCT CCA ATT GAT ACT ATC   363
97    I   T   V   S   S   G   N   D   I   T   F   T   L   P   S   S   P   I   D   T   I   116

364  GCA GCT GGA AAT GAC ATC ACG TTT ACT TTA CCA TCT TCT CCA ATT GAT GGT GAT ACT ATC   423
117   A   A   G   N   D   I   T   F   T   L   P   S   S   P   I   D   G   D   T   I   136

424  GTT CTC CAA GAT ATT GGA GGA AAA CCT GGA GTT AAC CAA GTT TTA ATT GTA GCT CCA GTA   483
137   V   L   Q   D   I   G   G   K   P   G   V   N   Q   V   L   I   V   A   P   V   156

484  CAA AGT ATT GTA AAC TTT AGA GGT GAA CAG CGT TCA GTA CTA ATG ACT CAT CCA AAG   543
157   Q   S   I   V   N   F   R   G   E   Q   R   S   V   L   M   T   H   P   K   176
```

FIG.7A

| | | | | | | | | | | | | | | | | | | | | |
|---|---|---|---|---|---|---|---|---|---|---|---|---|---|---|---|---|---|---|---|---|
|544|TCA|CAG|CTA|GTT|TTA|ATT|TTT|AGT|AAT|CCT|CTG|TGG|CAA|ATG|TAT|GTT|GCT|GAT|TAT|AGT|603|
|177|S|Q|L|V|L|I|F|S|N|R|L|W|Q|M|Y|V|A|D|Y|S|196|
|604|AGA|GAA|GCT|ATA|GTT|GTA|ACA|CCA|AAT|ACT|TAT|CAA|GCG|CAA|TCC|CAA|AAC|GAT|TTT|ATC|663|
|197|R|E|A|I|V|V|T|P|N|T|Y|Q|A|Q|S|Q|N|D|F|I|216|
|664|GTA|CGT|AGA|TTT|ACT|TCT|GCT|GCA|CCA|ATT|AAT|GTC|AAA|CTT|CCA|AGA|TTT|GCT|AAT|CAT|723|
|217|V|R|R|F|T|S|A|A|P|I|N|V|K|L|P|R|F|A|N|H|236|
|724|GGC|GAT|ATT|ATT|AAT|TTC|GTC|GAT|TTA|GAT|AAA|CTA|AAT|CCG|CTT|TAT|CAT|ACA|ATT|GTT|783|
|237|G|D|I|I|N|F|V|D|L|D|K|L|N|P|L|Y|H|T|I|V|256|
|784|ACT|ACA|TAC|GAT|GAA|ACG|TCA|GTA|CAA|GAA|GTT|GGA|ACT|CAT|TCC|ATT|GAA|GGC|CGT|843|
|257|T|T|Y|D|E|T|S|V|Q|E|V|G|T|H|S|I|E|G|R|276|
|844|ACA|TCG|ATT|GAC|GGT|TTC|TTG|ATG|TTT|GAT|GAT|AAT|GAG|AAA|TTA|TGG|AGA|CTG|TTT|GAC|903|
|277|T|S|I|D|G|F|L|M|F|D|D|N|E|K|L|W|R|L|F|D|296|
|904|GGG|GAT|AGT|AAA|GCG|CGT|TTA|CGT|ATC|ATA|ACG|ACT|AAT|TCA|AAC|ATT|CGT|CCA|AAT|GAA|963|
|297|G|D|S|K|A|R|L|R|I|I|T|T|N|S|N|I|R|P|N|E|316|
|964|GAA|GTT|ATG|GTA|TTT|GGT|GCG|AAT|AAC|GGA|ACA|ACT|CAA|ACT|CAA|ACA|ATT|GAG|CTT|AAG|CTT|CCA|1023|
|317|E|V|M|V|F|G|A|N|N|G|T|T|Q|T|Q|T|I|E|L|K|L|P|336|
|1024|ACT|AAT|ATT|TCT|GTT|GGT|GAT|ACT|GTT|AAA|ATT|TCC|ATG|AAT|TAC|ATG|AGA|AAA|GGA|CAA|1083|
|337|T|N|I|S|V|G|D|T|V|K|I|S|M|N|Y|M|R|K|G|Q|356|

FIG. 7B

```
1084  ACA GTT AAA ATC AAA GCT GCT GAT GAA GAT AAA ATT GCT TCT TCA GTT CAA TTG CTG CAA  1143
357    T   V   K   I   K   A   A   D   E   D   K   I   A   S   S   V   Q   L   L   Q   376

1144  TTC CCA AAA CGC TCA GAA TAT CCA CCT GAA GCT GAA TGG GTT ACA GTT CAA GAA TTA GTT  1203
377    F   P   K   R   S   E   Y   P   P   E   A   E   W   V   T   V   Q   E   L   V   396

1204  TTT AAC GAT GAA ACT AAT TAT CCA GTT TTG GAG CTT GCT TAC ATA GAA GAT TCT GAT  1263
397    F   N   D   E   T   N   Y   P   V   L   E   L   A   Y   I   E   D   S   D   416

1264  GGA AAA TAT TGG GTT GTA CAG CAA AAC GTT CCA ACT GTA GAA AGA GTA GAT TCT TTA AAT  1323
417    G   K   Y   W   V   V   Q   Q   N   V   P   T   V   E   R   V   D   S   L   N   436

1324  GAT TCT ACT AGA GCA AGA TTA GGC GTA ATT GCT TTA GCT ACA CAA GCT CAA GCT AAT GTC  1383
437    D   S   T   R   A   R   L   G   V   I   A   L   A   T   Q   A   Q   A   N   V   456

1384  GAT TTA GAA AAT TCT CCA CAA AAA GAA TTA GCA AGA ATA GCA ACT ACT CAA GAA ACC TTA GCT AAT CGT  1443
457    D   L   E   N   S   P   Q   K   E   L   A   I   T   P   E   T   L   A   N   R   476

1444  ACT GCT ACA GAA ACT CGC AGA GGT ATT GCA AGA ATA ACT ATC ATC ACT CCT AAA AAG CTG AAT GAA CAG  1503
477    T   A   T   E   T   R   R   G   I   A   R   I   T   I   I   T   P   K   K   L   N   E   Q   496

1504  AAC ACC ACA TTC TCT TTT GCT GAT GAT ATC ATC ATC ACT CCT AAA AAG CTG AAT GAA AGA  1563
497    N   T   T   F   S   F   A   D   D   I   I   I   T   P   K   K   L   N   E   R   516

1564  ACT GCT ACA GAA ACT CGT AGA GGT GTC GCA GAA ATT GCT GGA CAG CAA GAA ACT AAT GCA  1623
517    T   A   T   E   T   R   R   G   V   A   E   I   A   T   Q   Q   E   T   N   A   536
```

FIG.7C

| | | | | | | | | |
|---|---|---|---|---|---|---|---|---|
| 1624 | GGA | ACC | GAT | GAT | ACT | ACA | ATC | ATC ACT CCT AAA AAG CTT CAA GCT CGT CAA GGT TCT GAA | 1683 |
| 537 | G | T | D | D | T | T | I | I T P K K L Q A R Q G S E | 556 |
| 1684 | TCA | TTA | TCT | GGT | ATT | GTA | ACC | TTT GTA TCT ACT GCA GGT GCT CCA GCT TCT AGC CGT | 1743 |
| 557 | S | L | S | G | I | V | T | F V S T A G A P A S S R | 576 |
| 1744 | GAA | TTA | AAT | GGT | ACG | AAT | GTT | TAT AAT AAA AAC ACT GAT AAT TTA GTT GTT TCA CCT AAA | 1803 |
| 577 | E | L | N | G | T | N | V | Y N K N T D N L V V S P K | 596 |
| 1804 | GCT | TTG | GAT | CAG | TAT | AAA | GCT | ACT CCA CAA CAG CAA ACA CAG GGT GCA ATT TTA GCA GTT GAA | 1863 |
| 597 | A | L | D | Q | Y | K | A | T P T Q Q Q T Q G A V L A V E | 616 |
| 1864 | AGT | GAA | GTA | ATT | GCT | GGA | CAA | AGT CAG CAA CAG GGA TGG GCA AAT GCT GTT ACC CCA GAA | 1923 |
| 617 | S | E | V | I | A | G | Q | S Q Q Q G W A N A V T P E | 636 |
| 1924 | ACG | TTA | CAT | AAA | AAG | ACA | TCA | ACT GAT GGA AGA ATT GGT TTA ATT GAA ATT GCT ACG CAA | 1983 |
| 637 | T | L | H | K | K | T | S | T D G R I G L I E I A T Q | 656 |
| 1984 | AGT | GAA | GTT | AAT | ACA | GGA | ACT | GAT TAT ACT CGT GCA GTC ACT CCT AAA ACT TTA AAT GAC | 2043 |
| 657 | S | E | V | N | T | G | T | D Y T R A V T P K T L N D | 676 |
| 2044 | CGT | AGA | GCA | ACT | GAA | AGT | TTA | AGT GGT ATA GCT GAA ATT GCT ACA CAA GTT GAA TTC GAC | 2103 |
| 677 | R | R | A | T | E | S | L | S G I A E I A T Q V E F D | 696 |
| 2104 | GCA | GGC | GTC | GAC | GAT | ACT | CGT | ATC TCT ACA CCA TTA AAA ATT AAA ACC AGA TTT AAT AGT | 2163 |
| 697 | A | G | V | D | D | T | R | I S T P L K I K T R F N S | 716 |

FIG.7D

| | | | | | | | | | | |
|---|---|---|---|---|---|---|---|---|---|---|
| 2164 | ACT | GAT | CGT | ACT | TCT | GTT | GCT | CTA | TCT | GGA | TTA | GTT | GCT | CTA | TCT | GAA | TCA | GGA | ACT | CTC | TGG | GAC | 2223 |
| 717 | T | D | R | T | S | V | V | A | L | S | G | L | V | E | S | G | T | L | W | D | 736 |
| 2224 | CAT | TAT | ACA | CTT | AAT | ATT | GAA | GCA | AAT | GAG | ACA | CAA | CGT | GGT | ACA | CTT | CGT | GTA | GCT | 2283 |
| 737 | H | Y | T | L | N | I | L | E | A | N | E | T | Q | R | G | T | L | R | V | A | 756 |
| 2284 | ACG | CAG | GTC | GAA | GCT | GCG | GGA | ACA | TTA | GAT | AAT | GTT | TTA | ATA | ACT | CCT | AAA | AAG | CTT | 2343 |
| 757 | T | Q | V | E | A | A | G | T | L | D | N | V | L | I | T | P | K | K | L | 776 |
| 2344 | TTA | GGT | ACT | AAA | TCT | ACT | GAA | GCC | CAA | GAG | GGT | GTT | ATT | AAA | GTT | GCA | ACT | CAG | TCT | GAA | 2403 |
| 777 | L | G | T | K | S | T | E | A | Q | E | G | V | I | K | V | A | T | Q | S | E | 796 |
| 2404 | ACT | GTC | ACT | GGA | ACG | TCA | GCA | AAT | ACT | GCT | GTA | TCT | CCA | AAA | AAT | TTA | AAA | TGG | ATT | GCG | 2463 |
| 797 | T | V | T | G | T | S | A | N | T | A | V | S | P | K | N | L | K | W | I | A | 816 |
| 2464 | CAG | AGT | GAA | CCT | ACT | TGG | GCA | GCT | ACT | ACT | GCA | ATA | AGA | GGT | TTT | GTT | AAA | ACT | TCA | TCT | 2523 |
| 817 | Q | S | E | P | T | W | A | A | T | T | A | I | R | G | F | V | K | T | S | S | 836 |
| 2524 | GGT | TCA | ATT | ACA | TTC | GTT | GGT | AAT | GAT | ACA | GTC | GGT | TCT | ACC | CAA | GAT | TTA | GAA | CTG | TAT | 2583 |
| 837 | G | S | I | T | F | V | G | N | D | T | V | G | S | T | Q | D | L | E | L | Y | 856 |
| 2584 | GAG | AAA | AAT | AGC | TAT | GCC | GTA | TCA | CCA | TAT | GAA | TTA | AAC | CGT | GTA | TTA | GCA | AAT | TAT | TTG | 2643 |
| 857 | E | K | N | S | Y | A | V | S | P | Y | E | L | N | R | V | L | A | N | Y | L | 876 |
| 2644 | CCA | CTA | AAA | GCA | AAA | GCT | GAT | ACA | AAT | TTA | TTG | GAT | GGT | CTA | GAT | TCA | TCT | CAG | TTC | 2703 |
| 877 | P | L | K | A | K | A | D | T | N | L | L | D | G | L | D | S | S | Q | F | 896 |

FIG. 7E

| | | | | | | | | | | |
|---|---|---|---|---|---|---|---|---|---|---|
| 2704 | ATT | CGT | AGG | GAT | ATT | GCA | CAG | ACG | GTT | AAT | GGT | TCA | CTA | ACC | TTA | ACC | CAA | CAA | ACG | AAT | 2763 |
| 897 | I | R | R | D | I | A | Q | T | V | N | G | S | L | T | L | T | Q | Q | T | N | 916 |

| 2764 | CTG | AGT | GCC | CCT | CTT | GTA | TCA | TCT | AGT | ACT | GGT | GAA | TTT | GGT | GGT | TCA | TTG | GCC | GCT | AAT | 2823 |
| 917 | L | S | A | P | L | V | S | S | S | T | G | E | F | G | G | S | L | A | A | N | 936 |

| 2824 | AGA | ACA | ATC | CGT | AAT | ACA | GGA | GCC | CCG | ACT | AGT | ATC | GTT | TTC | GAA | AAA | GGT | CCT | 2883 |
| 937 | R | T | I | R | N | T | G | A | P | T | S | I | V | F | E | K | G | P | 956 |

| 2884 | GCA | TCC | GGG | GCA | AAT | CCT | GCA | CAG | TCA | ATG | AGT | ATT | CGT | GTA | TGG | GGT | AAC | CAA | TTT | GGC | 2943 |
| 957 | A | S | G | A | N | P | A | Q | S | M | S | I | R | V | W | G | N | Q | F | G | 976 |

| 2944 | GCC | CGT | AGT | GAT | ACC | CGT | TCC | ACA | GTG | TTT | GAA | GTT | GGC | GAT | GAC | ACA | TCT | CAT | CAC | 3003 |
| 977 | G | G | S | D | T | T | R | S | T | V | F | E | V | G | D | D | T | S | H | H | 996 |

| 3004 | TTT | TAT | TCT | CAA | CGT | AAT | AAA | GAC | GGT | AAT | ATA | GCC | TTT | AAC | ATT | AAT | GGT | ACT | GTA | ATG | 3063 |
| 997 | F | Y | S | Q | R | N | K | D | G | N | I | A | F | N | I | N | G | T | V | M | 1016 |

| 3064 | CCA | ATA | AAC | ATT | AAT | GCT | TCC | GGT | TTG | ATG | AAT | GTC | AAT | GGC | ACT | GCA | ACA | TTC | GGT | CGT | 3123 |
| 1017 | P | I | N | I | N | A | S | G | L | M | N | V | N | G | T | A | T | F | G | R | 1036 |

| 3124 | TCA | GTT | ACA | GCC | AAT | GGT | GAA | TTC | ATC | AGC | AAG | TCT | GCA | AAT | GCT | TTT | AGA | GCA | ATA | AAC | 3183 |
| 1037 | S | V | T | A | N | G | E | F | I | S | K | S | A | N | A | F | R | A | I | N | 1056 |

| 3184 | GGT | GAT | TAC | GGA | TTC | TTT | ATT | CGT | AAT | GAT | GCC | TCT | AAT | ACC | TAT | TTT | TTG | CTC | ACT | GCA | 3243 |
| 1057 | G | D | Y | G | F | F | I | R | N | D | A | S | N | T | Y | F | L | L | T | A | 1076 |

FIG. 7F

```
3244 GCC GGT GAT CAG ACT GGT GGT TTT AAT GGA TTA CGC CCA TTA TTA ATT AAT AAT CAA TCC 3303
1077  A   G   D   Q   T   G   G   F   N   G   L   R   P   L   L   I   N   N   Q   S  1096

3304 GGT CAG ATT ACA ATT GGT GAA GGC TTA ATC ATT GCC AAA GGT GTT ACT ATA AAT TCA GGC 3363
1097  G   Q   I   T   I   G   E   G   L   I   I   A   K   G   V   T   I   N   S   G  1116

3364 GGT TTA ACT GTT AAC TCC AGA ATT CGT TCT CAG GGT ACT AAA ACA TCT GAT TTA TAT ACC 3423
1117  G   L   T   V   N   S   R   I   R   S   Q   G   T   K   T   S   D   L   Y   T  1136

3424 CGT GCC CCA ACA TCT GAT ACT GTA GGA TTC TGG TCA ATC GAT ATT AAT GAT TCA GCC ACT 3483
1137  R   A   P   T   S   D   T   V   G   F   W   S   I   D   I   N   D   S   A   T  1156

3484 TAT AAC CAG TTC CCC GGT TAT TTT AAA ATG GTT GAA AAA ACT AAT GAA GTG ACT GGG CTT 3543
1157  Y   N   Q   F   P   G   Y   F   K   M   V   E   K   T   N   E   V   T   G   L  1176

3544 CCA TAC TTA GAA CGT GGC GAA GAA GTT AAA TCT CCT GGT ACA CTG ACT CAG TTT GGT AAC 3603
1177  P   Y   L   E   R   G   E   E   V   K   S   P   G   T   L   T   Q   F   G   N  1196

3604 ACA CTT GAT TCG CTT TAC CAA GAT TGG ATT ACT TAT CCA ACG ACG CCA GAA GCC CGT ACC 3663
1197  T   L   D   S   L   Y   Q   D   W   I   T   Y   P   T   T   P   E   A   R   T  1216

3664 ACT CGC TGG ACA CGT ACA TGG CAG AAA AAC TCT TGG TCA AGT TTT GTT CAG GTA 3723
1217  T   R   W   T   R   T   W   Q   K   N   S   W   S   S   F   V   Q   V  1236

3724 TTT GAC GGA GGT AAC CCT CCT CAA CCA CCA TCT GAT ATC GGT GCT TTA CCA TCT GAT AAT GCT 3783
1237  F   D   G   G   N   P   P   Q   P   P   S   D   I   G   A   L   P   S   D   N   A  1256
```

FIG.7G

```
3784 ACA ATG GGG AAT CTT ACT ATT CCT GAT TTC TTG CCA ATT GGT AAT GTT CGC ATT GTT CCT 3843
1257  T   M   G   N   L   T   I   P   D   F   L   R   I   G   N   V   R   I   V   P  1276

3844 GAC CCA GTG AAT AAA ACG GTT GAA TGG GTT GAA TTT GAA TAA GAGGTATT ATG GAA AAA TTT 3905
1277  D   P   V   N   K   T   V   E   W   V   E   F   E   *           M   E   K   F     4

3906 ATG GCC GAG ATT TGG ACA AGG ATA TGT CCA AAC GCC ATT TTA TCC GAA AGT AAT TCA GTA 3965
   5  M   A   E   I   W   T   R   I   C   P   N   A   I   L   S   E   S   N   S   V    24

3966 AGA TAT AAA ATA AGT GCG GGT TCT TGC CCG CTT TCT ACA GCA GGA CCA TCA TAT GTT 4025
  25  R   Y   K   I   S   I   A   G   S   C   P   L   S   T   A   G   P   S   Y   V    44

4026 AAA TTT CAG GAT AAT CCT GTA GGA AGT CAA ACA TTT AGG CGC AGG CCT TCA TTT AAG AGT 4085
  45  K   F   Q   D   N   P   V   G   S   Q   T   F   R   R   R   P   S   F   K   S    64

4086 TTT TGA CCCTTCCACCGGAGCATTAGTTGATAGTAAGTCAT ATG CTT TTT CGA CTT CAA ATG ATA CTA 4153
  65  F   *                                      M   L   F   R   L   Q   M   I   L     9

4154 CAT CAG CTG CTT TTG TTA GTT TTC ATG AAT TCT TTG ACG AAT AAT CGA ATT GTT GCT ATA 4213
  10  H   Q   L   L   L   L   V   F   M   N   S   L   T   N   N   R   I   V   A   I    29

4214 TTA ACT AGT GGA AAG GTT AAT TTT CCT CCT GAA GTA GTA TCT TGG TTA AGA ACC GCC GGA 4273
  30  L   T   S   G   K   V   N   F   P   P   E   V   V   S   W   L   R   T   A   G    49

4274 ACG TCT GCC TTT CCA TCT GAT TCT ATA TTG TCA AGA TTT GAC GTA TCA TAT GCT GCT TTT 4333
  50  T   S   A   F   P   S   D   S   I   L   S   R   F   D   V   S   Y   A   A   F    69
```

FIG. 7H

```
4334 TAT ACT TCT TCT AAA AGA GCT ATC GCA TTA GAG CAT GTT AAA CTG AGT AAT AGA AAA AGC 4393
  70  Y   T   S   S   K   R   A   I   A   L   E   H   V   K   L   S   N   R   K   S   89

4394 ACA GAT GAT TAT CAA ACT ATT TTA GAT GTT GTA TTT GAC AGT TTA GAA GAT GTA GGA GCT 4453
  90  T   D   D   Y   Q   T   I   L   D   V   V   F   D   S   L   E   D   V   G   A  109

4454 ACC GGG TTT CCA AGA AGA ACG TAT GAA AGT GTT GAG CAA TTC ATG TCG GCA GTT GGT GGA 4513
 110  T   G   F   P   R   R   T   Y   E   S   V   E   Q   F   M   S   A   V   G   G  129

4514 ACT AAT AAC GAA ATT GCG AGA TTG CCA ACT TCA GCT GCT ATA AGT AAA TTA TCT GAT TAT 4573
 130  T   N   N   E   I   A   R   L   P   T   S   A   A   I   S   K   L   S   D   Y  149

4574 AAT TTA ATT CCT GGA GAT GTT CTT TAT CTT AAA GCT CAG TTA TAT GCT GAT GCT GAT TTA 4633
 150  N   L   I   P   G   D   V   L   Y   L   K   A   Q   L   Y   A   D   A   D   L  169

4634 CTT GCT CTT GGA ACT ACA AAT ATA TCT ATC CGT TTT TAT AAT GCA TCT AAC GGA TAT ATT 4693
 170  L   A   L   G   T   T   N   I   S   I   R   F   Y   N   A   S   N   G   Y   I  189

4694 TCT TCA ACA CAA GCT GAA TTT ACT GGG CAA GCT GGA TCA TGG GAA TTA AAG GAA GAT TAT 4753
 190  S   S   T   Q   A   E   F   T   G   Q   A   G   S   W   E   L   K   E   D   Y  209

4754 GTA GTT GTT CCA GAA AAC GCA GTA GGA TTT ACG ATA TAC GCA CAG AGA ACT GCA CAA GCT 4813
 210  V   V   V   P   E   N   A   V   G   F   T   I   Y   A   Q   R   T   A   Q   A  229

4814 GGC CAA GGT GGC ATG AGA AAT TTA AGC TTT TCT GAA GTA TCA AGA AAT GGC GGC ATT TCG 4873
 230  G   Q   G   G   M   R   N   L   S   F   S   E   V   S   R   N   G   G   I   S  249
```

FIG. 71

```
4874  AAA CCT GCT GAA TTT GGC GTC AAT GGT ATT CGT GTT AAT TAT ATC TGC GAA TCC GCT TCA  4933
250     K   P   A   E   F   G   V   N   G   I   R   V   N   Y   I   C   E   S   A   S   269

4934  CCT CCG GAT ATA ATG GTA CTT CCT ACG CAA GCA TCG TCT AAA ACT GGT AAA GTG TTT GGG  4993
270     P   P   D   I   M   V   L   P   T   Q   A   S   S   K   T   G   K   V   F   G   289

4994  CAA GAA TTT AGA GAA GTT TAA ATTGAGGGACCCTCGGGTTCCCTTTTCTTTATAAATACTATTCAAATAAA  5066
290     Q   E   F   R   E   V   *                                                         296

5067  GGGCCATACA ATG GCT GAT TTA AAA GTA GGT TCA ACA ACT GGA GGC TCT GTC ATT TGG CAT  5127
                  M   A   D   L   K   V   G   S   T   T   G   G   S   V   I   W   H   17
              1

5128  CAA GGA AAT TTT CCA TTG AAT CCA GCC GGT GAC GAT GTA CTC TAT AAA TCA TTT AAA ATA  5187
 18     Q   G   N   F   P   L   N   P   A   G   D   D   V   L   Y   K   S   F   K   I    37

5188  TAT TCA GAA TAT AAC AAA CCA CAA GCT GTT TCT AAA GCT AAT GGT  5247
 38     Y   S   E   Y   N   K   P   Q   A   A   D   N   D   F   V   S   K   A   N   G    57

5248  GGT ACT TAT GCA TCA AAG GTA ACA TTT AAC GCT GGC ATT CAA GTC CCA TAT GCT CCA AAC  5307
 58     G   T   Y   A   S   K   V   T   F   N   A   G   I   Q   V   P   Y   A   P   N    77

5308  ATC ATG AGC CCA TGC GGG ATT TAT GGG GGT AAC GGT GAT GGT GCT ACT TTT GAT AAA GCA  5367
 78     I   M   S   P   C   G   I   Y   G   G   N   G   D   G   A   T   F   D   K   A    97

5368  AAT ATC GAT ATT GTT TCA TGG TAT GGC GTA GGA TTT AAA TCG TCA TTT GGT TCA ACA GGC  5427
 98     N   I   D   I   V   S   W   Y   G   V   G   F   K   S   S   F   G   S   T   G   117
```

FIG. 7J

```
5428 CGA ACT GTT GTA ATT AAT ACA CGC AAT GGT GAT ATT AAC ACA AAA GGT GTT GTG TCG GCA  5487
 118  R   T   V   V   I   N   T   R   N   G   D   I   N   T   K   G   V   V   S   A   137

5488 GCT GGT CAA GTA AGA AGT GGT GCG GCT CCT ATA GCA GCG AAT GAC CTT ACT AGA AAG        5547
 138  A   G   Q   V   R   S   G   A   A   P   I   A   A   N   D   L   T   R   K        157

5548 GAC TAT GTT GAT GGA GCA ATA ACT GTT ACT GCA AAT TCT AGG GTG CTA CGG                5607
 158  D   Y   V   D   G   A   I   T   V   T   A   N   S   R   V   L   R                177

5608 TCT GGT GAC ACC ATG ACA CCG AAT TTA ACA GCG CCA AAC TTT TTC TCG CAG AAT CCT GCA    5667
 178  S   G   D   T   M   T   P   N   L   T   A   P   N   F   F   S   Q   N   P   A    197

5668 TCT CAA CCC TCA CAC GTT CCA CGA TTT GAC CAA ATC GTA ATT AAG GAT TCT GTT CAA GAT    5727
 198  S   Q   P   S   H   V   P   R   F   D   Q   I   V   I   K   D   S   V   Q   D    217

5728 TTC GGC TAT TAT TAA GAGGACTT ATG GCT ACT TTA AAA CAA ATA CAA TTT AAA AGA AGC AAA   5789
 218  F   G   Y   Y   *              M   A   T   L   K   Q   I   Q   F   K   R   S   K  13

5790 ATC GCA GGA ACA CGT CCT GCT GCT TCA GTA TTA GCC GAA GGT GAA TTG GCT ATA AAC TTA    5849
  14  I   A   G   T   R   P   A   A   S   V   L   A   E   G   E   L   A   I   N   L     33

5850 AAA GAT AGA ACA ATT TTT ACT AAA GAT GAT GAT TCA GGA AAT ATC ATC GAT CTA GGT TTT GCT 5909
  34  K   D   R   T   I   F   T   K   D   D   D   S   G   N   I   I   D   L   G   F   A  81

5910 AAA GGC GGG CAA GTT GAT GCC AAC GTT ACT ATT AAC GGA CTT TTG AGA TTA AAT GGC GAT    5969
  54  K   G   G   Q   V   D   A   N   V   T   I   N   G   L   L   R   L   N   G   D     73
```

FIG.7K

```
5970 TAT GTA CAA ACA GGT GGA ATG ACT GTA AAC GGA CCC ATT GGT TCT ACT GAT GGC GTC ACT 6029
  74  Y   V   Q   T   G   G   M   T   V   N   G   P   I   G   S   T   D   G   V   T   93

6030 GGA AAA ATT TTC AGA TCT ACA CAG GGT TCA TTT TAT GCA AGA GCA ACA AAC GAT ACT TCA 6089
  94  G   K   I   F   R   S   T   Q   G   S   F   Y   A   R   A   T   N   D   T   S  113

6090 AAT GCC CAT TTA TGG TTT GAA AAT GCC GAT GGC ACT GAA CCT GGC GTT ATA TAT GCT CGC 6149
 114  N   A   H   L   W   F   E   N   A   D   G   T   E   R   G   V   I   Y   A   R  133

6150 CCT CAA ACT ACA GAC GGT GAA ATA CGC CTT AGG GTT ACA CAA GGA ACA GGA AGC ACT 6209
 134  P   Q   T   T   D   G   E   I   R   L   R   V   R   Q   G   T   G   S   T  153

6210 GCC AAC AGT GAA TTC TAT TTC CCC TCT ATA AAT GGA GGC GAA TTT CAG GCT AAC CGT ATT 6269
 154  A   N   S   E   F   Y   F   P   S   I   N   G   G   E   F   Q   A   N   R   I  173

6270 TTA GCA TCA GAT TCG TTA GTA ACA AAA CGC ATT GCC GTT GAT ACC GTT ATT CAT GAT GCC 6329
 174  L   A   S   D   S   L   V   T   K   R   I   A   V   D   T   V   I   H   D   A  193

6330 AAA GCA TTT GGA CAA TAT CTT CGT AAA GTT CGC GCT AAG TCC GGT GGT ACA ATT TAT 6389
 194  K   A   F   G   Q   Y   D   S   H   S   L   V   N   Y   Y   P   G   T   G  213

6390 GAA ACA AAT GGT GTA AAC TAT CTT CGT AAA GTT CGC GCT AAG TCC GGT GGT ACA ATT TAT 6449
 214  E   T   N   G   V   N   Y   L   R   K   V   R   A   K   S   G   G   T   I   Y  911

6450 CAT GAA ATT GTT ACT GCA CAA ACA GGC CTG GCT GAT GAA GTT TCT TGG TGG TCT GGT GAT 6509
 234  H   E   I   V   T   A   Q   T   G   L   A   D   E   V   S   W   W   S   G   D  253
```

FIG.7L

```
6510  ACA CCA GTA TTT AAA CTA TAC GGT ATT CGT GAC GAT GGC AGA ATG ATT ATC CGT AAT AGC  6569
 254   T   P   V   F   K   L   Y   G   I   R   D   D   G   R   M   I   I   R   N   S    273

6570  CTT GCA TTA GGT ACA TTC ACT ACA AAT TTC CCG TCT AGT GAT TAT GGC AAC GTC GGT GTA  6629
 274   L   A   L   G   T   F   T   T   N   F   P   S   S   D   Y   G   N   V   G   V    293

6630  ATG GGC GAT AAG TAT CTT GTT CTC GGC GAC ACT GTA ACT GCC TTG TCA TAC AAA AAA ACT  6689
 294   M   G   D   K   Y   L   V   L   G   D   T   V   T   A   L   S   Y   K   K   T    313

6690  GGT GTA TTT GAT CTA GTT GGC GGT GGA TAT TCT GTT GCT TCT ATT ACT CCT GAC AGT TTC  6749
 314   G   V   F   D   L   V   G   G   G   Y   S   V   A   S   I   T   P   D   S   F    333

6750  CGT AGT ACT CGG AAA GGT ATA TTT GGT CGT TCT GAG GAC CAA GGC GCA ACT TGG ATA ATG  6809
 334   R   S   T   R   K   G   I   F   G   R   S   E   D   Q   G   A   T   W   I   M    353

6810  CCT GGT ACA AAT GCT CTC TTG TCT GTT CAA ACA CAA GCT GAT AAT AAC AAT AAC GCT GGA  6869
 354   P   G   T   N   A   L   L   S   V   Q   T   Q   A   D   N   N   N   N   A   G    373

6870  GAC GGA CAA ACC CAT ATC GGG TAC AAT GCT GGC AAA ATG GAA ATT AAC CCG TAT TTC CGT GGT  6929
 374   D   G   Q   T   H   I   G   Y   N   A   G   G   K   M   N   H   Y   F   R   G    393

6930  ACA GGT CAG ATG AAT ATC AAT ACC CAA CAA GGT ATG GAA ATT AAC CCG GGT ATT TTG AAA  6989
 394   T   G   Q   M   N   I   N   T   Q   Q   G   M   E   I   N   P   G   I   L   K    413

6990  TTG GTA ACT GGC TCT AAT AAT GTA CAA TTT TAC GCT GAC GGA ACT ATT TCT TCC ATT CAA  7049
 414   L   V   T   G   S   N   N   V   Q   F   Y   A   D   G   T   I   S   S   I   Q    433
```

FIG.7M

```
7050  CCT ATT AAA TTA GAT AAC GAG ATA TTT TTA ACT AAA TCT AAT AAT ACT GCG GGT CTT AAA  7109
434    P   I   K   L   D   N   E   I   F   L   T   K   S   N   N   T   A   G   L   K   453

7110  TTT GGA GCT CCT AGC CAA GTT GAT GGC ACA AGG ACT ATC CAA TGG AAC GGT GGT ACT CGC  7169
454    F   G   A   P   S   Q   V   D   G   T   R   T   I   Q   W   N   G   G   T   R   473

7170  GAA GGA CAG AAT AAA AAC TAT GTG ATT ATT AAA GCA TGG GGT AAC TCA TTT AAT GCC ACT  7229
474    E   G   Q   N   K   N   Y   V   I   I   K   A   W   G   N   S   F   N   A   T   493

7230  GGT GAT AGA TCT CGC GAA ACG GTT TTC CAA GTA TCA GAT AGT CAA GGA TAT TAT TTT TAT  7289
494    G   D   R   S   R   E   T   V   F   Q   V   S   D   S   Q   G   Y   Y   F   Y   513

7290  GCT CAT CGT AAA GCT CCA ACC GGC GAC GAA ACT ATT GGA CGT ATT GAA GCT CAA TTT GCT  7349
514    A   H   R   K   A   P   T   G   D   E   T   I   G   R   I   E   A   Q   F   A   533

7350  GGG GAT GTT TAT GCT AAA GGT ATT ATT GCC AAC GGA AAT TTT AGA GTT GTT GGG TCA AGC  7409
534    G   D   V   Y   A   K   G   I   I   A   N   G   N   F   R   V   V   G   S   S   553

7410  GCT TTA GCC GGC AAT GTT ACT ATG TCT AAC GGT TTG TTT GTC CAA GGT GGT TCT TCT ATT  7469
554    A   L   A   G   N   V   T   M   S   N   G   L   F   V   Q   G   G   S   S   I   573

7470  ACT GGA CAA GTT AAA ATT GGC GGA ACA GCA AAC GCA CTG AGA ATT TGG AAC GCT GAA TAT  7529
574    T   G   Q   V   K   I   G   G   T   A   N   A   L   R   I   W   N   A   E   Y   593

7530  GGT GCT ATT TTC CCT CGT TCG GAA AGT GAA AGT GAA AGT GAA AGC TTT TAT ATT CCA ACC AAT CAA AAT GAA  7589
594    G   A   I   F   R   R   S   E   S   N   F   Y   I   I   P   T   N   Q   N   E   613
```

FIG.7N

```
7590 GGA GAA AGT GGA GAC ATT CAC AGC TCT TTG AGA CCT GTG AGA ATA GGA TTA AAC GAT GGC 7649
 614  G   E   S   G   D   I   H   S   S   L   R   P   V   R   I   G   L   N   D   G   633

7650 ATG GTT GGG TTA GGA AGA GAT TCT TTT ATA GTA GAT CAA AAT AAT GCT TTA ACT ACG ATA 7709
 634  M   V   G   L   G   R   D   S   F   I   V   D   Q   N   N   A   L   T   T   I   653

7710 AAC AGT AAC TCT CGC ATT AAT GCC AAC TTT AGA ATG CAA TTG GGG CAG TCG GCA TAC ATT 7769
 654  N   S   N   S   R   I   N   A   N   F   R   M   Q   L   G   Q   S   A   Y   I   673

7770 GAT GCA GAA TGT ACT GAT GCT GTT CGC CCG GGT GCA GGT TCA TTT GCT TCC CAG AAT 7829
 674  D   A   E   C   T   D   A   V   R   P   A   G   S   F   A   S   Q   N   693

7830 AAT GAA GAC GTC CGT GCC CCG TTC TAT ATG AAT ATT GAT AGA ACT GAT GCT AGT GCA TAT 7889
 694  N   E   D   V   R   A   P   F   Y   M   N   I   D   R   T   D   A   S   A   Y   713

7890 GTT CCT ATT TTG AAA CAA CGT TAT GTT CAA GGC AAT GGC TGC TAT TCA TTA GGG ACT TTA 7949
 714  V   P   I   L   K   Q   R   Y   V   Q   G   N   G   C   Y   S   L   G   T   L   733

7950 ATT AAT AAT GGT AAT TTC CGA GTT CAT TAC CAT GGC GGA GAT AAC GGT TCT ACA GGT 8009
 734  I   N   N   G   N   F   R   V   H   Y   H   G   G   D   N   G   S   T   G   753

8010 CCA CAG ACT GCT GAT TTT GGA TGG GAA TTT ATT AAA AAC GGT GAT TTT ATT TCA CCT CGC 8069
 754  P   Q   T   A   D   F   G   W   E   F   I   K   N   G   D   F   I   S   P   R   773

8070 GAT TTA ATA GCA GGC AAA GTC AGA TTT GAT AGA ACT GGT AAT ATC ACT GGT GGT TCT GGT 8129
 774  D   L   I   A   G   K   V   R   F   D   R   T   G   N   I   T   G   G   S   G   793
```

FIG. 70

```
8130 AAT TTT GCT AAC TTA AAC AGT ACA ATT GAA TCA CTT AAA ACT GAT ATC ATG TCG AGT TAC 8180
 794  N   F   A   N   L   N   S   T   I   E   S   L   K   T   D   I   M   S   S   Y   813

8190 CCA ATT GGT GCT CCG ATT CCT TGC CCG AGT GAT TCA GTT CCT GCT GGA TTT GCT TTG ATG 8249
 814  P   I   G   A   P   I   P   W   P   S   D   S   V   P   A   G   F   A   L   M   833

8250 GAA GGT CAG ACC TTT GAT AAG TCC GCA TAT CCA AAG TTA GCT GTT GCA TAT CCT AGC GGT 8309
 834  E   G   Q   T   F   D   K   S   A   Y   P   K   L   A   V   A   Y   P   S   G   853

8310 GTT ATT CCA GAT ATG CGC GGG CAA ACT ATC AAG GGT AAA CCA AGT GGT CGT GCT GTT TTG 8369
 854  V   I   P   D   M   R   G   Q   T   I   K   G   K   P   S   G   R   A   V   L   873

8370 AGC GCT GAG GCA GAT GGT GTT AAG GCT CAT AGC CAT AGT GCA TCG GCT TCA AGT ACT GAC 8429
 874  S   A   E   A   D   G   V   K   A   H   S   H   S   A   S   T   D   893

8430 TTA GGT ACT AAA ACC ACA TCA AGC TTT GAC TAT GGT ACC AAG GGA ACT AAC AGT ACG GGT 8489
 894  L   G   T   K   T   T   S   S   F   D   Y   G   T   K   G   T   N   S   T   G   913

8490 GGA CAC ACT CAC TCT GGT AGT GGT TCT ACT AGC ACA AAT GGT GAG CAC AGC CAC TAC ATC 8549
 914  G   H   T   H   S   G   S   G   S   T   S   T   N   G   E   H   S   H   Y   I   933

8550 GAG GCA TGG AAT GGT ACT GTA GGT GGT AAT AAG ATG TCA TCA TAT GCC ATA TCA TAC 8609
 934  E   A   W   N   G   T   V   G   G   N   K   M   S   S   Y   A   I   S   Y   953

8610 AGG GCC GGT GGG AGT AAC ACT AAT GCA GCA GGG AAC CAC AGT CAC ACT TTC TCT TTT GGG 8669
 954  R   A   G   G   S   N   T   N   A   A   G   N   H   S   H   T   F   S   F   G   973
```

FIG.7P

```
8670  ACT AGC AGT GCT GCC GAC CAT TCC CAC TCT GTA GGT ATT GGT GCT CAT ACC CAC ACG GTA  8729
974    T   S   S   A   G   D   H   S   H   S   V   G   I   G   A   H   T   H   T   V    993

8730  GCA ATT GGA TCA CAT GGT CAT ACT ATC ACT GTA AAT AGT ACA GGT AAT ACA GAA AAC ACC  8789
994    A   I   G   S   H   G   H   T   I   T   V   N   S   T   G   N   T   E   N   T   1013

8790  GTT AAA AAC ATT GCT TTT AAC TAT ATC GTT CGT TTA GCA TAA GGAGAGGGCCTTCGGCCCTTCTAA  8855
1014   V   K   N   I   A   F   N   Y   I   V   R   L   A   *                            1027
```

FIG.7Q

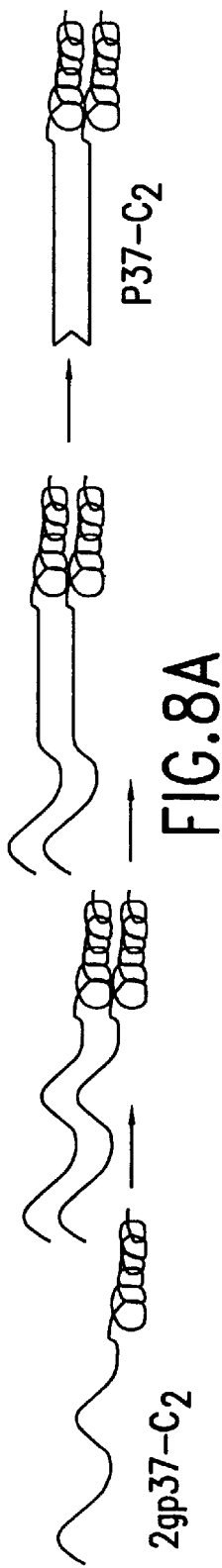
FIG. 8A
FIG. 8B
FIG. 9

MATERIALS FOR THE PRODUCTION OF NANOMETER STRUCTURES AND USE THEREOF

This application is a divisional of Ser. No. 08/542,003, filed Oct. 12, 1995, now U.S. Pat. No. 5,864,013, which is a continuation-in-part of application Ser. No. 08/322,760 filed Oct. 13, 1994, now U.S. Pat. No. 5,877,279, which is incorporated by reference herein in its entirety.

This invention was made with Government support under Grant No. MCB 9308834 awarded by the National Science Foundation. The Government has certain rights in this invention.

FIELD OF THE INVENTION . . .
BACKGROUND TO THE INVENTION . . .
SUMMARY OF THE INVENTION . . .
BRIEF DESCRIPTION OF THE DRAWINGS . . .
DETAILED DESCRIPTION OF THE INVENTION . . .
DEFINITIONS . . .
STRUCTURAL UNITS . . .
DESIGN AND PRODUCTION OF THE ROD PROTEINS . . .
ASSEMBLY OF INDIVIDUAL ROD COMPONENTS INTO NANOSTRUCTURES . . .
STRUCTURAL COMPONENTS FOR SELF ASSEMBLY OF BEAMS IN VITRO . . .
APPLICATIONS . . .
KITS . . .
EXAMPLE 1: DESIGN, CONSTRUCTION AND EXPRESSION OF INTERNALLY DELETED P37 . . .
EXAMPLE 2: DESIGN, CONSTRUCTION AND EXPRESSION OF A gp37-36 CHIMER . . .
EXAMPLE 3: MUTATION OF THE GP37-36 CHIMER TO PRODUCE COMPLEMENTARY SUPPRESSORS . . .
EXAMPLE 4: DESIGN, CONSTRUCTION AND EXPRESSION OF A gp36-34 CHIMER . . .
EXAMPLE 5: ISOLATION OF THERMOLABILE PROTEINS FOR SELF-ASSEMBLY . . .
EXAMPLE 6: ASSEMBLY OF ONE-DIMENSIONAL RODS . . .
EXAMPLE 7: STAGED ASSEMBLY OF POLYGONS . . .

FIELD OF THE INVENTION

The present invention pertains to nanostructures, i.e., nanometer sized structures useful in the construction of microscopic and macroscopic structures. In particular, the present invention pertains to nanostructures based on bacteriophage T4 tail fiber proteins and variants thereof.

BACKGROUND TO THE INVENTION

While the strength of most metallic and ceramic based materials derives from the theoretical bonding strengths between their component molecules and crystallite surfaces, it is significantly limited by flaws in their crystal or glass-like structures. These flaws are usually inherent in the raw materials themselves or developed during fabrication and are often expanded due to exposure to environmental stresses.

The emerging field of nanotechnology has made the limitations of traditional materials more critical. The ability to design and produce very small structures (i.e., of nanometer dimensions) that can serve complex functions depends upon the use of appropriate materials that can be manipulated in predictable and reproducible ways, and that have the properties required for each novel application.

Biological systems serve as a paradigm for sophisticated nanostructures. Living cells fabricate proteins and combine them into structures that are perfectly formed and can resist damage in their normal environment. In some cases, intricate structures are created by a process of self-assembly, the instructions for which are built into, the component polypeptides. Finally, proteins are subject to proofreading processes that insure a high degree of quality control.

Therefore, there is a need in the art for methods and compositions that exploit these unique features of proteins to form constituents of synthetic nanostructures. The need is to design materials whose properties can be tailored to suit the particular requirements of nanometer-scale technology. Moreover, since the subunits of most macrostructural materials, ceramics, metals, fibers, etc., are based on the bonding of nanostructural subunits, the fabrication of appropriate subunits without flaws and of exact dimensions and uniformity should improve the strength and consistency of the macrostructures because the surfaces are more regular and can interact more closely over an extended area than larger, more heterogeneous material.

SUMMARY OF THE INVENTION

In one aspect, the present invention provides isolated protein building blocks for nanostructures, comprising modified tail fiber proteins of bacteriophage T4. The gp34, 36, and 37 proteins are modified in various ways to form novel rod structures with different properties. Specific internal peptide sequences may be deleted without affecting their ability to form diners and associate with their natural tail fiber partners. Alternatively, they may be modified so that they: interact only with other modified, and not native, tail fiber partners; exhibit thermolabile interactions with their partners; or contain additional functional groups that enable them to interact with heterologous binding moieties.

The present invention also encompasses fusion proteins that contain sequences from two or more different tail fiber proteins. The gp35 protein, which forms an angle joint, is modified so as to form average angles different from the natural average angle of 137° (±7°) or 156° (±12°), and to exhibit thermolabile interactions with its partners.

In another aspect, the present invention provides nanostructures comprising native and modified tail fiber proteins of bacteriophage T4. The nanostructures may be one-dimensional rods, two-dimensional polygons or open or closed sheets, or three-dimensional open cages or closed solids.

BRIEF DESCRIPTION OF THE DRAWINGS

FIGS. 6A–6D show the DNA sequence (SEQ ID NO:1) of genes 34, 35, 36, and 37 of bacteriophage T4.

FIGS. 7A–Q show the amino acid sequences (shown in single-letter codes) of the gene products of genes 34 (SEQ ID NO:2, ORFX SEQ ID NO:3), 35 (SEQ ID NO:4), 36 (SEQ ID NO:5), and 37 (SEQ ID NO:6) of bacteriophage T4. The amino acid sequences (bottom line of each pair) are aligned with the nucleotide sequences (top line of each pair.) It is noted that the deduced protein sequence of gene 35 (from NCBI database) is not believed to be accurate.

FIGS. 8A–8B show a schematic representation of: the formation of a P37 dimer initiator from a molecule that self-assembles into a dimer (FIG. 8A); and the formation of a P37 trimer initiator from a molecule that self-assembles into a trimer (FIG. 8B).

FIG. 9 shows a schematic representation of the formation of the polymer (P37-36)n with an initiator that is a self-assembling dimer.

DETAILED DESCRIPTION OF THE INVENTION

Figure 1A:
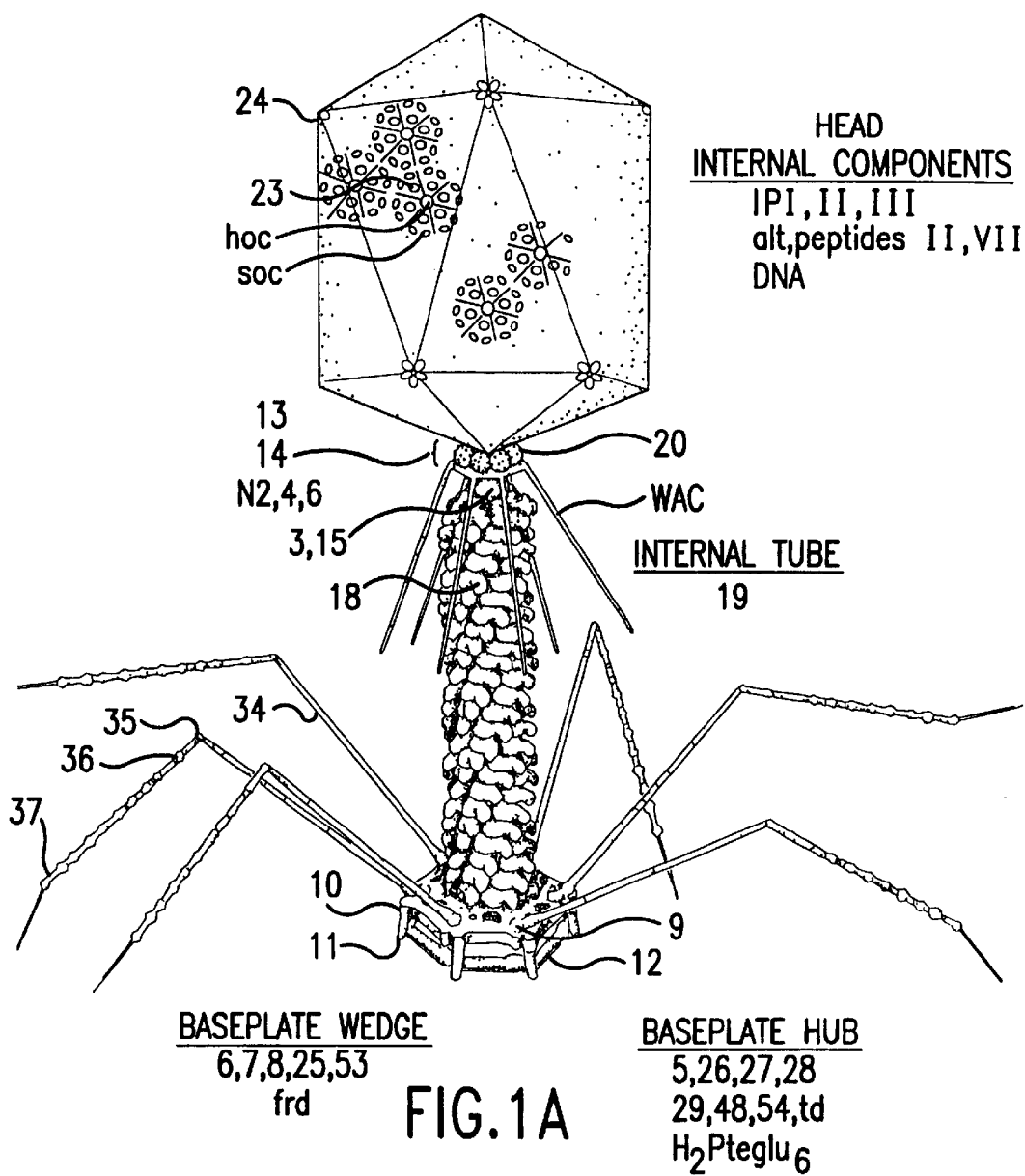
FIGS. 1A and 1B show a schematic representation of the T4 bacteriophage particle (FIG. 1A), and a schematic representation of the T4 bacteriophage tail fiber (FIG. 1B).

All patents, patent applications and literature references cited in the specification are hereby incorporated by reference in their entirety. In the case of inconsistencies, the present disclosure, including, definitions, will prevail.

Although the invention is described in terms of bacteriophage T4 tail fiber proteins, it will be understood, that the invention is also applicable to tail fiber proteins of other T-even-like phage, e.g., of the T4 family (e.g., T4, TuIa, TuIb), and T2 family (T2, T6, K3, Ox2, M1, etc.)

DEFINITIONS

"Nanostructures" are defined herein as structures of different sizes and shapes that are assembled from nanometer-sized protein components.

"Chimers" are defined herein as chimeric proteins in which at least the amino- and carboxy-terminal regions are derived from different original polypeptides, whether the original polypeptides are naturally occurring or have been modified by mutagenesis.

"Homodimers" are defined herein as assemblies of two substantially identical protein subunits that form a defined three-dimensional structure.

The designation "gp" denotes a monomeric polypeptide, while the designation "P" denotes homooligomers. P34, P36, and P37 are presumably homodimers or homotrimers.

An isolated polypeptide that "consists essentially of" a specified amino acid sequence is defined herein as a polypeptide having the specified sequence or a polypeptide that contains conservative substitutions within that sequence. Conservative substitutions, as those of ordinary skill in the art would understand, are ones in which an acidic residue is replaced by an acidic residue, a basic residue by a basic residue, or a hydrophobic residue by a hydrophobic residue. Also encompassed is a polypeptide that lacks one or more amino acids at either the amino terminus or carboxy terminus, up to a total of five at either terminus, when the absence of the particular residues has no discernable effect on the structure or the function of the polypeptide in practicing the present invention.

The present invention pertains to a new class of protein building blocks whose dimensions are measured in nanometers, which are useful in the construction of microscopic and macroscopic structures. Without wishing to be bound by theory, it is believed that the basic unit is a homodimer composed of two identical protein subunits having a cross-β configuration, although a trimeric structure is also possible. Thus, as will be apparent, references to a "homodimer" or "dimerization" as used herein will in many instances be construed as also referring to a homotrimer or trimerization. These long, stiff, and stable rod-shaped units can assemble with other rods using coupling devices that can be attached genetically or in vitro. The ends of one rod may attach to different ends of other rods or similar rods. Variations in the length of the rods, in the angles of attachment, and in their flexibility characteristics permit differently-shaped structures to self-assemble in situ. In this manner the units can self-assemble into predetermined larger structures of one, two or three dimensions. The self-assembly can be staged to form structures of precise dimensions and uniform strength due to the flawless biological manufacture of the components. The rods can also be modified by genetic and chemical modifications to form predetermined specific attachment sites for other chemical entities, allowing the formation of complex structures.

An important aspect of the present invention is that the protein units can be designed so that they comprise rods of different lengths, and can be further modified to include features that alter their surface properties in predetermined ways and/or influence their ability to join with other identical or different units. Furthermore, the self-assembly capabilities can be expanded by producing chimeric proteins that combine the properties of two different members of this class. This design feature is achieved by manipulating the structure of the genes encoding these proteins.

As detailed below, the compositions and methods of the present invention take advantage of the properties of the natural proteins, i.e., the resulting structures are stiff, strong, stable in aqueous media, heat resistant, protease resistant, and can be rendered biodegradable. A large quantity of units can be fabricated easily in microorganisms. Furthermore, for ease of automation, large quantities of parts and subassemblies can be stored and used as needed.

The sequences of the protein subunits are based on the components of the tail fiber of the T4 bacteriophage of E. coli. It will be understood that the principles and techniques can be applied to the tail fibers of other T-even phages, or other related bacteriophages that have similar tail and/or fiber structures.

Figure 1B:
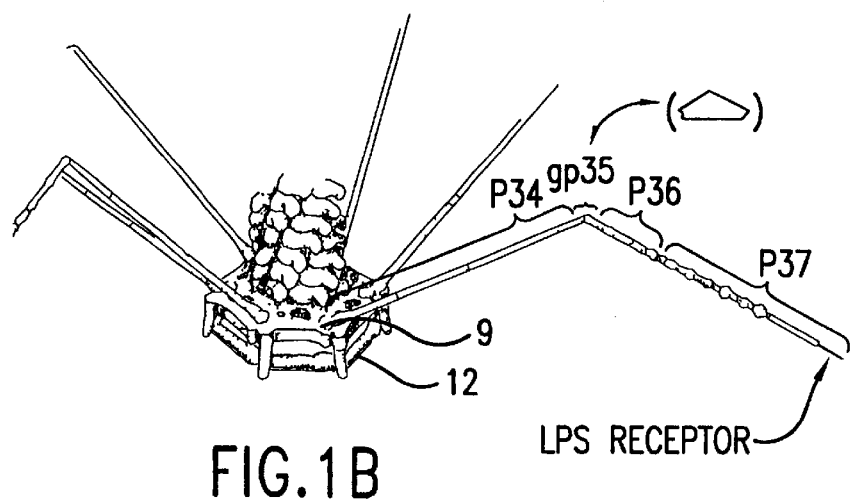

The structure of the T4 bacteriophage tail fiber (illustrated in FIGS. 1A–1B) can be represented schematically as follows (N=amino terminus, C=carboxy terminus): N[P34]C—N[gp35]C—N[P36]C—N[P37]C. P34, P36, and P37 are all stiff, rod-shaped protein homodimers in which two identical β sheets, oriented in the same direction, are fused face-to-face by hydrophobic interactions between the sheets juxtaposed with a 180° rotational axis of symmetry through the long axis of the rod. (The structure will vary if P34, P36, and P37 are homotrimers.) gp35, by contrast, is a monomeric polypeptide that attaches specifically to the N-terminus of P36 and then to the C-terminus of P34 and forms an angle joint between two rods. During T4 infection of E. coli, two gp37 monomers dimerize to form a P37 homodimer; the process of dimerization is believed to initiate near the C-terminus of P37 and to require two E. coli chaperon proteins. (A variant gp37 with a temperature sensitive mutation near the C-terminus used in the present invention requires only one chaperon, gp57, for dimerization.) Once dimerized, the N-terminus of P37 initiates the dimerization of two gp36 monomers to a P36 rod. The joint between the C-terminus of P36 and the N-terminus of P37 is tight and stiff but noncovalent. The N-terminus of P36 then attaches to a gp35 monomer; this interaction stabilizes P36 and forms the elbow of the tail fiber. Finally, gp35 attaches to the C-terminus of P34 (which uses gp57 for dimerization). Thus, self assembly of the tail fiber is regulated by a predetermined order of interaction of specific subunits whereby structural maturation caused by formation of the first subassembly permits interaction with new (previously disallowed) subunits. This results in the production of a structure of exact specifications from a random mixture of the components.

In accordance with the present invention, the genes encoding these proteins may be modified so as to make rods of different lengths with different combinations of ends. The properties of the native proteins are particularly advantageous in this regard. First, the β-sheet is composed of antiparallel β-strands with β-bends at the left (L) and right (R) edges. Second, the amino acid side chains alternate up and down out of the plane of the sheet. The first property allows bends to be extended to form symmetric and specific attachment sites between the L and R surfaces, as well as to form attachment sites for other structures. In addition, the core sections of the β-sheet can be shortened or lengthened by genetic manipulations e.g., by splicing DNA regions encoding β-bends, on the same edge of the sheet, to form new bends that exclude intervening peptides, or by inserting segments of peptide in an analogous manner by splicing at bend angles. The second property allows amino acid side chains extending above and below the surface of the β-sheet to be modified by genetic substitution or chemical coupling. Importantly, all of the above modifications are achieved without compromising the structural integrity of the rod. It will be understood by one skilled in the art that these properties allow a great deal of flexibility in designing units that can assemble into a broad variety of structures, some of which are detailed below.

STRUCTURAL UNITS

Figures 2, 3A, 3B:
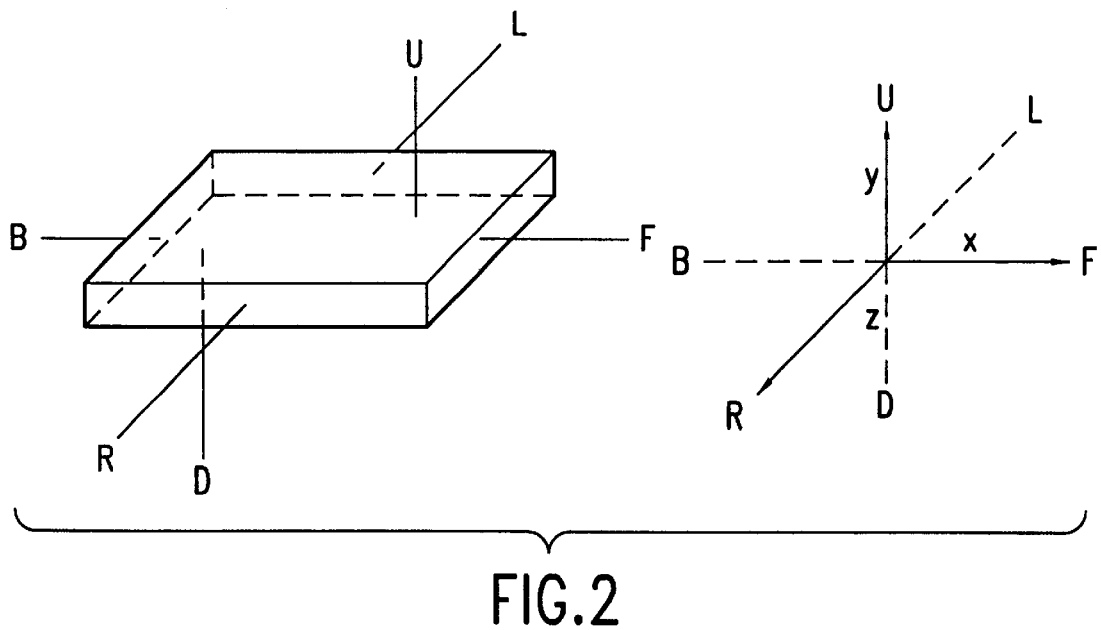
FIG. 2 shows a schematic representation of a unit rod.
FIGS. 3A–3D show schematic representations of: a one-dimensional multi-unit rod joined along the x axis (FIG. 3A); closed simple sheets (FIG. 3B); closed brickwork sheets (FIG. 3C); and open brickwork sheets (FIG. 3D).

The rods of the present invention function like wooden 2×4 studs or steel beams for construction. In this case, the surfaces are exactly reproducible at the molecular level and thereby fitted for specific attachments to similar or different units rods at fixed joining sites. The surfaces are also modified to be more or less hydrophilic, including positively or negatively charged groups, and have protrusions built in for specific binding to other units or to an intermediate joint with two receptor sites. The surfaces of the rod and a schematic of the unit rod are illustrated in FIG. 2. The three dimensions of the rod are defined as: x, for the back (B) to front (F) dimension; y, for the down (D) to up (U) dimension; and z, for the left (L) to right (R) dimension.

One dimensional multi-unit rods can be most readily assembled from single unit rods joined along the x axis (FIG. 3A) but regular joining of subunits in either of the other two dimensions will also form a long structure, but with different cross sections than in the x dimension.

Figure 3C:
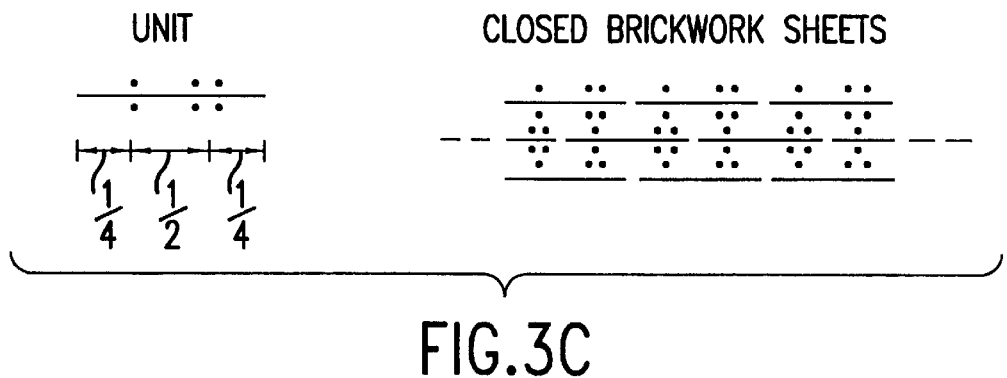
Figure 3D:
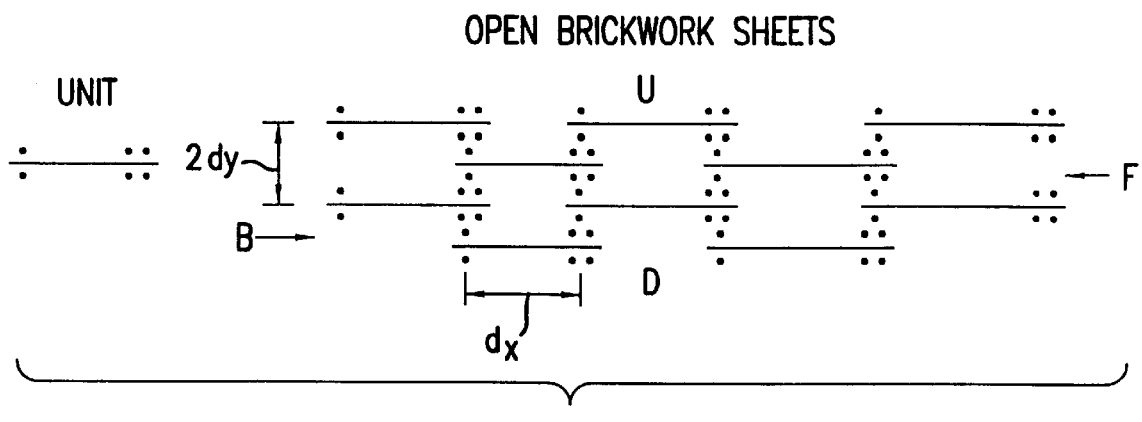

Two dimensional constructs are sheets formed by interaction of rods along any two axes. 1) Closed simple sheets are formed from surfaces which overlap exactly, along any two axes (FIG. 3B). 2) Closed brickwork sheets are formed from interaction between units that have exactly overlapping surfaces in one dimension and a special type of overlap in the other (FIG. 3C). In this case there must be two different sets of complementary joints spaced with exactly ½ unit distance between them. If they are centered (i.e., each set ¼ from the end) then each joint will be in the center of the units above and below. If they are offset, then the joint will be offset as well. In this construction, the complementary interacting sites are schematized by • and ••. If the interacting sites are each symmetric, the alternating rows can interact with the rods in either direction. If they are not symmetric, and can only interact with interacting rows facing in the same or opposite direction, the sheet will made of unidirectional rods or layers of rods in alternating directions. 3) Open brickwork sheets (or nets) result when the units are separated by more than one-half unit (FIG. 3D). The dimensions of the openings (or pores) depend upon the distance (dx) separating the interacting sites and the distance (dy) by which these sites separate the surfaces.

Figure 4:
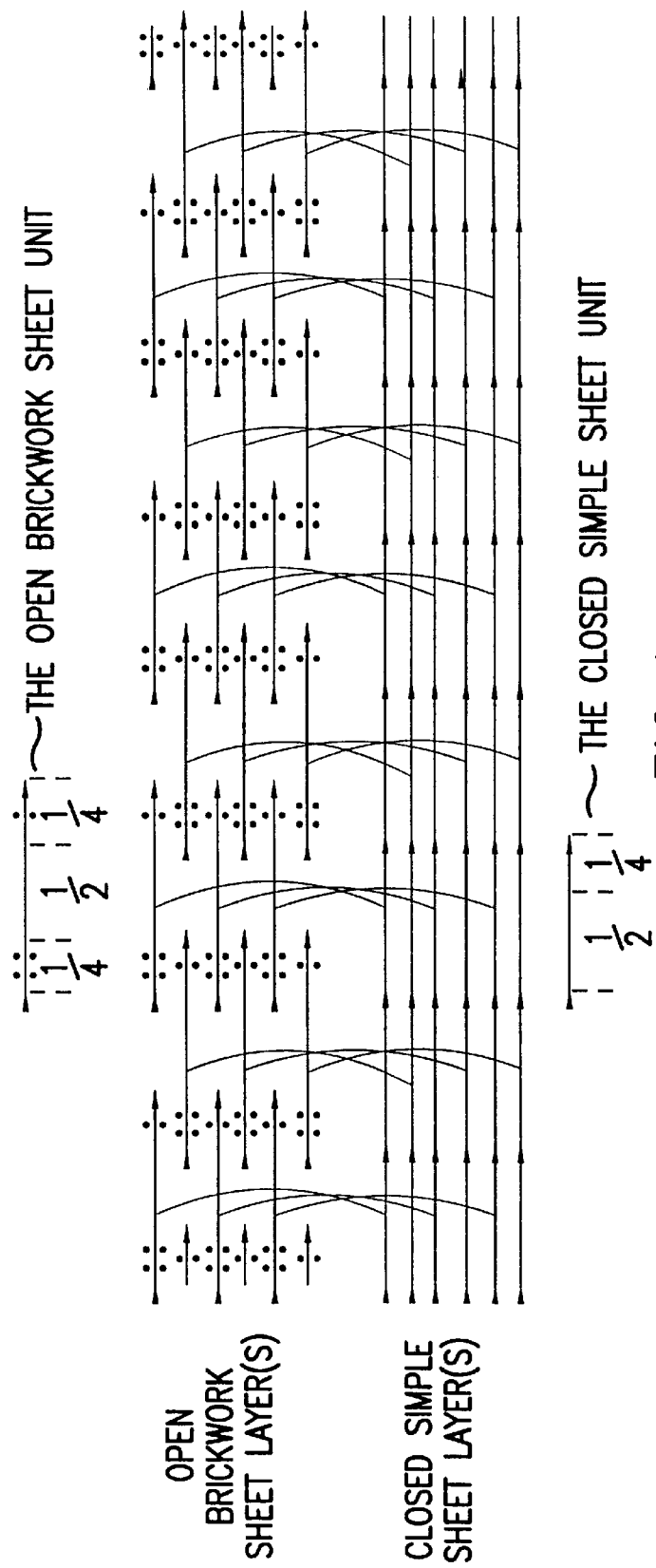
FIG. 4 shows a schematic representation of two units used to construct porous and solid sheets (top and bottom), which, when alternatively layered, produce a multi-tiered set of cages as shown.

Three dimensional constructs require sterically compatible interactions between all three surfaces to form solids. 1) Closed solids can assemble from units that overlap exactly in all three dimensions (e.g., the exact overlapping of closed simple sheets). In an analogous manner, closed brickwork sheets can form closed solids by overlapping sheets exactly or displaced to bring the brickwork into the third dimension. This requires an appropriate set of joints on all three pairs of parallel faces of the unit. 2) Porous solids are made by joining open brickwork sheets in various ways. For example, if the units overlap exactly in the third dimension, a solid is formed with the array of holes of exact dimensions running perpendicular to the plane of the paper. If instead, a material is needed with closed spaces, with layers of width dz (i.e., in the U→>D dimension), a simple closed sheet is layered on the open brickwork sheet to close the openings. If the overlap of the open brickwork sheet is e.g., ¼ unit, then a rod of length ¾ units is used to make the sheet. Joints are then needed in the z dimension. The two units used to polymerize these alternate layers, and the layers themselves, are schematized in FIG. 4.

Figure 5:
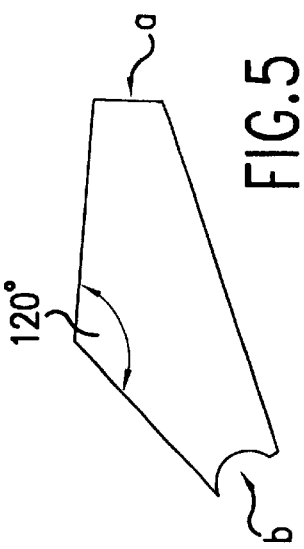
FIG. 5 shows a schematic representation of an angled structure having an angle of 120°.

All of the above structures are composed of simple linear rods. A second unit, the angle unit, expands the type and dimensionality of possible structures. The angle unit connects two rods at angles different from 180°, akin to an angle iron. The average angle and its degree of rigidity are built into this connector structure. For example, the structure shown in FIG. 5 has an angle of 120° and different specific joining sites at a and at b. The following are examples of structures that are formed utilizing angle joints:

1) Open brickwork sheets are expanded and strengthened in the direction normal to the rod direction by adding angles perpendicular to the sheet. In this case, a three dimensional network forms. Attachment of 90° angles to the ends of the rods makes an angle almost in the plane of the sheet, allowing new rods added to those angles (which must have some play out of the plane of the original sheet to attach in the first place) to form a new sheet, almost parallel, with an orientation normal to its upper or lower neighbor.

2) Hexagons are made from a mixture of rods and angle joints that form 120° angles. In this case, there are two exclusive sets of joints. Each set is made up of one of the two ends of the rod and one of the two complementary sites on the angle. This is a linear structure in the sense that the hexagon has a direction (either clockwise or counterclockwise). It can be made into a two dimensional open net (i.e., a two dimensional honeycomb) by joining the sides of the hexagons. It can form hexagonal tubes by joining the top of the hexagon below to the bottom face of the hexagon above. If the tubes also join by their sides, they will form an open three dimensional multiple hexagonal tube.

3) Helical hexagonal tubes are made analogously to hexagons but the sixth unit is not joined to the first to close the hexagon. Instead, the end is displaced from the plane of the hexagon and the seventh and further units are added to form a hexagonal tube which can be a spring if there is little or no adhesive force between the units of the helix, or a stiff rod if there is such a force to maintain the close proximity of apposing units.

It will be apparent to one skilled in the art that the compositions and methods of the present invention also encompass other polygonal structures such as octagons, as well as open solids such as tetrahedrons and icosahedrons formed from triangles and boxes formed from squares and rectangles. The range of structures is limited only by the types of angle units and the substituents that can be engineered on the different axes of the rod units. For example, other naturally occurring angles are found in the fibers of bacteriophage T7, which has a 90° angle (Steven et al., *J. Mol. Biol.* 200: 352–365, 1988).

DESIGN AND PRODUCTION OF THE ROD PROTEINS

The protein subunits that are used to construct the nanostructures of the present invention are based on the four polypeptides that comprise the tail fibers of bacteriophage T4, i.e., gp34, gp35, gp36 and gp37. The genes encoding these proteins have been cloned, and their DNA and protein sequences have been determined (for gene 36 and 37 see Oliver et al. *J. Mol. Biol.* 153: 545–568, 1981). The DNA and amino acid sequences of genes 34, 35, 36 and 37 are set forth in FIGS. 6A–D and 7A–D below.

Gp34, gp35, gp36, and gp37 are produced naturally following infection of *E. coli* cells by intact T4 phage particles. Following synthesis in the cytoplasm of the bacterial cell, the gp34, 36, and 37 monomers form homodimers, which are competent for assembly into maturing phage particles. Thus, *E. coli* serves as an efficient and convenient factory for synthesis and dimerization of the protein subunits described herein below.

In practicing the present invention, the genes encoding the proteins of interest (native, modified, or recombined) are incorporated into DNA expression vectors that are well known in the art. These circular plasmids typically contain selectable marker genes (usually conferring antibiotic resistance to transformed bacteria), sequences that allow replication of the plasmid to high copy number in *E. coli*, and a multiple cloning site immediately downstream of an inducible promoter and ribosome binding site. Examples of commercially available vectors suitable for use in the present invention include the pET system (Novagen, Inc., Madison, Wis.) and Superlinker vectors pSE280 and pSE380 (Invitrogen, San Diego, Calif.).

The strategy is to 1) construct the gene of interest and clone it into the multiple cloning site; 2) transform *E. coli* cells with the recombinant plasmid; 3) induce the expression of the cloned gene; 4) test for synthesis of the protein product; and, finally, 5) test for the formation of functional homodimers. In some cases, additional genes are also cloned into the same plasmid, when their function is required for dimerization of the protein of interest. For example, when wild-type or modified versions of gp37 are expressed, the bacterial chaperon gene 57 is also included; when wild-type or modified gp36 is expressed, the wild-type version or a modified version of the gp37 gene is included. The modified gp37 should have the capacity to dimerize and contain an N-terminus that can chaperon the dimerization of gp36. This method allows the formation of monomeric gene products and, in some cases, maturation of monomers to homodimeric rods in the absence of other phage-induced proteins normally present in a T4-infected cell.

Steps 1–4 of the above-defined strategy are achieved by methods that are well known in the art of recombinant DNA technology and protein expression in bacteria. For example, in step 1, restriction enzyme cleavage at multiple sites, followed by ligation of fragments, is used to construct deletions in the internal rod segment of gp34, 36, and 37 (see Example 1 below). Alternatively, a single or multiple restriction enzyme cleavage, followed by exonuclease digestion (EXO-SIZE, New England Biolabs, Beverly, Mass.), is used to delete DNA sequences in one or both directions from the initial cleavage site; when combined with a subsequent ligation step, this procedure produces a nested set of deletions of increasing sizes. Similarly, standard methods are used to recombine DNA segments from two different tail fiber genes, to produce chimeric genes encoding fusion proteins (called "chimers" in this description). In general, this last method is used to provide alternate N- or C-termini and thus create novel combinations of ends that enable new patterns of joining of different rod segments. A representative of this type of chimer, the fusion of gp37-36, is described in Example 2. The preferred hosts for production of these proteins (Step 2) is *E. coli* strain BL21(DE3) and BL21(DE3/pLysS) (available commercially from Novagen, Madison, Wis.), although other compatible recA strains, such as HMS174(DE3) and HMS174(DE3/pLysS) can be used. Transformation with the recombinant plasmid (Step 2) is accomplished by standard methods (Sambrook, *J., Molecular Cloning*, Cold Spring Harbor Laboratories, Cold Spring Harbor, N.Y.; this is also the source for standard recombinant DNA methods used in this invention.) Transformed bacteria are selected by virtue of their resistance to antibiotics e.g., ampicillin or kanamycin. The method by which expression of the cloned tail fiber genes is induced (Step 3) depends upon the particular promoter used. A preferred promoter is plac (with a laci$^q$ on the vector to reduce background expression), which can be regulated by the addition of isopropylthiogalactoside (IPTG). A second preferred promoter is pT7φ10, which is specific to T7 RNA polymerase and is not recognized by *E. coli* RNA polymerase. T7 RNA polymerase, which is resistant to rifamycin, is encoded on the defective lambda DE lysogen in the *E. coli* BL21 chromosome. T7 polymerase in BL21 (DE3) is super-repressed by the laci$^q$ gene in the plasmid and is induced and regulated by IPTG.

Typically, a culture of transformed bacteria is incubated with the inducer for a period of hours, during which the synthesis of the protein of interest is monitored. In the present instance, extracts of the bacterial cells are prepared, and the T4 tail fiber proteins are detected, for example, by SDS-polyacrylamide gel electrophoresis.

Once the modified protein is detected in bacterial extracts, it is necessary to ascertain whether or not it forms appropriate homodimers (Step 4). This is accomplished initially by testing whether the protein is recognized by an antiserum specific to the mature dimerized form of the protein.

Tail fiber-specific antisera are prepared as described (Edgar, R. S. and Lielausis, I., *Genetics* 52: 1187, 1965; Ward et al, *J. Mol. Biol.* 54:15, 1970). Briefly, whole T4 phage are used as an immunogen; optionally, the resulting antiserum is then adsorbed with tail-less phage particles, thus removing all antibodies except those directed against the tail fiber proteins. In a subsequent step, different aliquots of the antiserum are adsorbed individually with extracts that each lack a particular tail fiber protein. For example, if an extract containing only tail fiber components P34, gp35, and gp36 (derived from a cell infected with a mutant T4 lacking a functional gp37 gene) is used for absorption, the resulting antiserum will recognize only mature P37 and dimerized P36-P37. A similar approach may be used to prepare individual antisera that recognize only mature (i.e., homodimerized) P34 and P36 by adsorbing with extracts containing distal half tail fibers or P34, gp35 and P37, respectively. An alternative is to raise antibody against purified tail fiber halves, e.g., P34 and gp35-P36-P37. Anti gp35-P36-P37 can then be adsorbed with P36-P37 to produce anti-gp35, and anti-P36 can be produced by adsorption with P37 and gp35. Anti-P37, anti-gp35, and anti-P34 can also be produced directly by using purified P37, gp35, and P34 as immunogens. Another approach is to raise specific monoclonal antibodies against the different tail fiber components or segments thereof.

Specific antibodies to subunits or tail parts are used in any of the following ways to detect appropriately homodimerized tail fiber proteins: 1) Bacterial colonies are screened for those expressing mature tail fiber proteins by directly transferring the colonies, or, alternatively, samples of lysed or unlysed cultures, to nitrocellulose filters, lysing the bacterial cells on the filter if necessary, and incubating with specific antibodies. Formation of immune complexes is then detected by methods widely used in the art (e.g., secondary antibody conjugated to a chromogenic enzyme or radiolabelled Staphylococcal Protein A.). This method is particularly useful to screen large numbers of colonies e.g., those produced by EXO-SIZE deletion as described above. 2) Bacterial cells expressing the protein of interest are first metabolically labelled with $^{35}$S-methionine, followed by preparation of extracts and incubation with the antiserum. The immune complexes are then recovered by incubation with immobilized Protein A followed by centrifugation, after which they may be resolved by SDS-polyacrylamide gel electrophoresis.

An alternative competitive assay for testing whether internally deleted tail fiber proteins that do not permit phage infection nonetheless retain the ability to dimerize and associate with their appropriate partners utilizes an in vitro, complementation system. 1) A bacterial extract containing the modified protein of interest, as described above, is mixed with a second extract prepared from cells infected with a T4 phage that is mutant in the gene of interest. 2) After several hours of incubation, a third extract is added that contains the wild-type version of the protein being tested, and incubation is continued for several additional hours. 3) Finally, the extract is titered for infectious phage particles by infecting *E. coli* and quantifying the phage plaques that result. A modified tail fiber protein that is correctly dimerized and able to join with its partners is incorporated into tail fibers in a non-functional manner in Step 1, thereby preventing the incorporation of the wild-type version of the protein in Step 2; the result is a reduction in the titer of the resulting phage sample. By contrast, if the modified protein is unable to dimerize and thus form proper N- and/or C-termini, it will not be incorporated into phage particles in Step 1, and thus will not compete with assembly of intact phage particles in Step 2; the phage titer should thus be equivalent to that observed when no modified protein is added in Step 1 (a negative control.)

Another way in which to test whether chimers and internally deleted tail fiber proteins retain the ability to dimerize and associate with their appropriate partners is done in vivo. The assay detects the ability of such chimers and deleted proteins to compete with normal phage parts for assembly, thus reducing the burst size of a wild-type phage infecting the same host cell in which the chimers or deleted proteins are recombinantly expressed. Thus, expression from an expression vector encoding the chimer or deleted protein is induced inside a cell, which cell is then infected by a wild-type phage. Inhibition of wild-type phage production demonstrates the ability of the recombinant chimer or protein to associate with the appropriate tail fiber proteins of the phage.

The above-described methods are used, alone and in combination, in the design and production of different types of modified tail fiber proteins. For example, a preliminary screen of a large number of bacterial colonies for those expressing a properly dimerized protein will identify positive colonies, which can then be individually tested by in vitro complementation.

Non-limiting examples of novel proteins that are encompassed by the present invention include:

1) Internally deleted gp34, 36, and 37 polypeptides (See Example 1 below);
2) A C-terminally truncated gp36 fused to the N-terminus of N-terminally truncated gp37;
3) A fusion between gp36 and gp37 in which gp37 is N-terminal to gp36 (i.e., in reverse of the natural order), termed herein "gp37-36 chimer" (See Example 2 below);
4) A fusion between gp34 and gp36 in which gp36 is N-terminal to gp34 (i.e., in reverse of the natural order), termed herein "gp36-34 chimer";
5) A variant of gp36 in which the C-terminus is mutated such that it lacks the capability to interact with (and dimerize in response to) the N-terminus of wild-type P37, termed herein "gp36*";
6) A variant of gp37 in which the N-terminus is mutated such that it forms a P37 that lacks the capability to interact with the C-terminus of wild-type gp36, termed herein "*P37";
7) Variants of gp36* and *P37 that can interact with each other, but not with gp36 or P37.
8) A variant "P37-36 chimer" in which the gp36 moiety is derived from the variant as in 5), i.e., "P37-36*". (For 5–8, See Example 3 below.)
9) A variant "P37-36 chimer" in which the gp37 moiety is derived from the variant as in 6) above, i.e., "*P37-36".
10) A variant P37-36 chimer, *P37-P36*, in which the gp36 and gp37 moieties are derived from the variants in 7).
11) A fusion between gp36 and gp34 in which gp36 sequences are placed N-terminal to gp34, the dimer of which is termed herein "P36-34 chimer";
12) Variants of gp35 that form average angles different from 137° or 158° (the native angle) e.g., less than about 125° or more than about 145° under conditions wherein the wild-type gp35 protein forms an angle of 137° when combined with the P34 and P36-P37 dimers, and/or exhibit more or less flexibility-than the native polypeptide;
13) Variants of gp34, 35, 36 and 37 that exhibit thermolabile interactions or other variant specific interactions with their-cognate partners; and
14) Variants of gp37 in which the C-terminal domain of the polypeptide is modified to include sequences that confer specific binding properties on the entire molecule, e.g., sequences derived from avidin that recognize biotin, sequences derived from immunoglobulin heavy chain that recognize Staphylococcal A protein, sequences derived from the Fab portion of the heavy chain of monoclonal antibodies to which their respective Fab light chain counterparts could attach and form an antigen-binding site, immunoactive sequences that recognize specific antibodies, or sequences that bind specific metal ions. These ligands may be immobilized to facilitate purification and/or assembly.

In specific embodiments, the chimers of the invention comprise a portion consisting of at least the first 10 (N-terminal) amino acids of a first tail fiber protein fused via a peptide bond to a portion consisting of at least the last 10 (C-terminal) amino acids of a second tail fiber protein. The first and second tail fiber proteins can be the same or different proteins. In another embodiment, the chimers comprise an amino acid portion in the range of the first 10–60 amino acids from a tail fiber protein fused to an amino acid portion in the range of the last 10–60 amino acids from a second tail fiber protein. In another embodiment, each amino acid portion is at least 20 amino acids of the tail fiber protein. The chimers comprise portions, i.e., not full-length tail fiber proteins, fused to one another. In a preferred aspect, the first tail fiber protein portion of the chimer is from gp37, and the second tail fiber protein portion is from gp36. Such a chimer (gp37-36 chimer), after oligomerization to form P37-36, can polymerize to other identical oligomers. A gp36-34 chimer, after oligomerization to form P36-34, can bind to gp35, and this unit can then polymerize. In another embodiment, the first portion is from gp37, and the second portion is from gp34. In a preferred aspect, the chimers of the invention are made by insertions or deletions within a β turn of the β structure of the tail fiber proteins. Most preferably, insertions into a tail fiber sequence, or fusing to another tail fiber protein sequence, (preferably via manipulation at the recombinant DNA level to produce the desired encoded protein) is done so that sequences in β turns on the same edge of the β-sheet are joined.

In addition to the above-described chimers, nanostructures of the invention can also comprise tail fiber protein deletion constructs that are truncated at one end, e.g., are lacking an amino- or carboxy- end (of at least 5 or 10 amino acids) of the molecule. Such molecules truncated at the amino-terminus, e.g., of truncated gp37, gp34, or gp36, can be used to "cap" a nanostructure, since, once incorporated, they will terminate polymerization. Such molecules preferably comprise a fragment of a tail fiber protein lacking at least the first 10, 20, or 60 amino terminal amino acids.

In order to change the length of the rod component proteins as desired, portions of the same or different tail fiber proteins can be inserted into a tail fiber chimer to lengthen the rod, or be deleted from a chimer, to shorten the rod.

ASSEMBLY OF INDIVIDUAL ROD COMPONENTS INTO NANOSTRUCTURES

Expression of the proteins of the present invention in *E. coli* as described above results in the synthesis of large quantities of protein, and allows the simultaneous expression and assembly of different components in the same cells. The methods for scale-up of recombinant protein production are straightforward and widely known in the art, and many standard protocols can be used to recover native and modified tail fiber proteins from a bacterial culture.

In a preferred embodiment, native (nonrecombinant) gp35 is isolated for use by growing up a bacteriophage T4 having an amber mutation in-gene 36, in a su° bacterial strain (not an amber suppressor), and isolating gp35 from the resulting culture by standard methods.

P34, P36-P37, P37, and chimers derived from them are purified from *E. coli* cultures as mature dimers. Gp35 and variants thereof are purified as monomers. Purification is achieved by the following procedures or combinations thereof, using standard methods: 1) chromatography on molecular sieve, ion-exchange, and/or hydrophobic matrices; 2) preparative ultracentrifugation; and 3) affinity chromatography, using as the immobilized ligand specific antibodies or other specific binding moieties. For example, the C-terminal domain of P37 binds to the lipopolysaccharide of *E. coli* B. Other T4-like phages have P37 analogues that bind other cell surface components such as OmpF or TSX protein. Alternatively, if the proteins have been engineered to include heterologous domains that act as ligands or binding sites, the cognate partner is immobilized on a solid matrix and used in affinity purification. For example, such a heterologous domain can be biotin, which binds to a streptavidin-coated solid phase.

Alternatively, several components are co-expressed in the same bacterial cells, and sub-assemblies of larger nanostructures are purified subsequent to limited in vivo assembly, using the methods enumerated above.

The purified components are then combined in vitro under conditions where assembly of the desired nanostructure occurs at temperatures between about 4° C. and about 37° C., and at pHs between about 5 and about 9. For a given nanostructure, optimal conditions for assembly (i.e., type and concentration of salts and metal ions) are easily determined by routine experimentation, such as by changing each variable individually and monitoring formation of the appropriate products.

Alternatively, one or more crude bacterial extracts may be prepared, mixed, and assembly reactions allowed to proceed prior to purification.

In some cases, one or more purified components assemble spontaneously into the desired structure, without the necessity for initiators. In other cases, an initiator is required to nucleate the polymerization of rods or sheets. This offers the advantage of localizing the assembly process (i.e., if the initiator is immobilized or otherwise localized) and of regulating the dimensions of the final structure. For example, rod components that contain a functional P36 C-terminus require a functional P37 N-terminus to initiate rod formation stoichiometrically; thus, altering the relative amount of initiator and rod component will influence the average length of rod polymer. If the ratio is n, the average rod will be approximately (P37-36)n-N-terminus P37-P37 C-terminus.

In still other cases, the final nanostructure is composed of two or more components that cannot self-assemble individually but only in combination with each other. In this situation, alternating cycles of assembly can be staged to produce final products of precisely defined structure (see Example 6B below.)

When an immobilized initiator is used, it may be desirable to remove the polymerized unit from the matrix after staged assembly. For this purpose specialized initiators are engineered so that the interaction with the first rod component is rendered reversibly thermolabile (see Example 5 below). In this way, the polymer can be easily separated from the matrix-bound initiator, thereby permitting: 1) easy preparation of stock solutions of uniform parts or subassemblies, and 2) re-use of the matrix-bound initiator for multiple cycles of polymer initiation, growth, and release.

In an embodiment in which a nanostructure is assembled that is attached to a solid matrix via gp34 (or P34), one way in which to detach the nanostructure to bring it into solution is to use a mutant (thermolabile) gp34 that can be made to detach upon exposure to a higher temperature (e.g., 40° C.). Such a mutant gp34, termed T4 tsB45, having a mutation at its C-terminal end such that P34 attaches to the distal tail fiber half at 30° C. but can be separated from it in vitro by incubation at 40° C. in the presence of 1% SDS (unlike wild-type T4 which are stable under these conditions), has been reported (Seed, 1980, Studies of the Bacteriophage T4 Proximal Half Tail Fiber, Ph.D. Thesis, California Institute of Technology), and can be used.

Proteins which catalyze the formation of correct (lowest energy) stable secondary (2°) structure of proteins are called chaperone proteins. (Often, especially in globular proteins, this stabilization is aided by tertiary structure, e.g., stabilization of β-sheets by their interaction in β-barrels or by interaction with α-helices). Normally chaperonins prevent intrachain or interchain interactions which would produce untoward metastable folding intermediates and prevent or delay proper folding. There are two known accessory proteins, gp57 and gp38, in the imorphogenesis of T4 phage tail fibers which are sometimes called chaperoning because they are essential for proper maturation of the protein oligomers but are not present in the final structures.

The usual chaperonin system (e.g., groEL/ES) interact with certain oligopeptide moieties of the gene product to prevent unwanted interactions with oligopeptide moieties elsewhere on the same polypeptide or another peptide. These would form metastable folding intermediates which retard or prevent proper folding of the polypeptide to its native (lower energy) state.

Gp57, probably in conjunction with some membrane protein(s), has the role of juxtaposing (and aligning) and/or initiating the folding of 2 or 3 identical gp37 molecules. The aligned peptides then zip up (while mutually stabilizing their nascent β-structures) to form a beam, without further interaction with gp57. Gp57 acts in T4 assembly not only for oligomerization of gp37 but also for gp34 and gp12.

STRUCTURAL COMPONENTS FOR SELF ASSEMBLY OF BEAMS IN VITRO

Alternatively to starting the polymerization of chimers with the use of a preformed chimeric or natural oligomeric unit called an initiator produced in vivo, molecules (preferably peptides) that can self-assemble can be produced as fusion proteins, fused to the N- or C-terminus of tail fiber variants of the invention (chimers, deletion/insertion constructs) to align their ends and thus to facilitate their subsequent unaided folding into oligomeric, stable β-folded rod-like (beam) units in vitro, in the absence of the normally required chaperonin proteins (e.g., gp57) and host cell membrane proteins.

As an illustration, consider the P37 unit as an initiator of gp37-36 oligomerization and polymerization. Normally, proper folding of gp37 to a P37 initiator requires a phage infected cell membrane, and two chaperone proteins, gp38 and gp57. In a preferred embodiment, the need for gp38 can be obviated by use of a mutation, ts3813 (a duplication of 7 residues just downstream of the transition zone of gp37) which suppresses gene 38 (Wood, W. B., F. A. Eiserling and R. A. Crowther, 1994, "Long Tail Fibers: Genes, Proteins, Structure, and Assembly," in *Molecular Biology of Bacteriophage T4*, (Jim D. Karam, Editor) American Society for Microbiology, Washington, D.C., pp 282–290). If a moiety that self-assembles into a dimer or trimer or other oligomer ("self-assembling moiety") is fused to a C-terminal deletion of gp37 downstream or upstream of the transition region [the transition region is a conserved 17 amino acid residue region in T4-like tail fiber proteins where the structure of the protein narrows to a thin fiber; see Henning et al., 1994, "Receptor recognition by T-even-type coliphages," in *Molecular Biology of Bacteriophage T4*, Karam (ed.), American Society for Microbiology, Washington, D.C., pp. 291–298; Wood et al., 1994, "Long tail fibers: Genes, proteins, structure, and assembly," in *Molecular Biology of Bacteriophage T4*, Karam (ed.), American Society for Microbiology, Washington, D.C., pp. 282–290], when it is expressed, the self-assembling moiety will oligomerize in parallel and thus align the fused gp37 peptides, permitting them to fold in vitro, in the absence of other chaperonin proteins.

If P37 is a dimer (FIG. 8A), the self-assembling moiety can be a self dimerizing peptide such as the leucine zipper, made from residues 250–281 from the yeast transcription factor, GCN4 (E. K. O'Shea, R. Rutkowski and P. S. Kim, Science 243:538, 1989) or the self dimerizing mutant leucine zipper peptide, pIL in which the a positions are substituted with isoleucine and the d positions with leucine (Harbury P. B., T. Zhang, P. S. Kim and T. Alper. 1993. A Switch Between Two-, Three-, and Four-Stranded Coiled Coils in GCN4 Leucine Zipper Mutants. Science, 262:1401–1407). If P37 is a trimer (FIG. 8B), the self-assembling moiety can be a self trimerizing mutant leucine zipper peptide, pII in which both the a and d positions are substituted with isoleucine (Harbury P. B., et al. ibid). Alternatively, a collagen peptide can be used as the self-assembling moiety, such as that described by Bella et al. (J. Bella, M. Eaton, B. Brodsky and H. M. Berman. 1994. Crystal and Molecular Structure of a Collagen-Like Peptide at 1.9 Å Resolution. Science, 226:75–81), which self aligns by an inserted specific non repeating alanine residue near the center.

Self-assembling moieties can be used to make initiators for polymerizations in the absence of the normal initiators. For example, to create an initiator for oligomerization and polymerization of the chimeric monomer, gp37-36, gp37-36-$C_2$ can be used as illustrated in FIG. 9. ($C_2$ means that a dimer forming peptide is fused to the C-terminus of the gp36 moiety. This is used if the beam is a dimeric structure. Otherwise $C_3$—a trimer forming peptide fused to the C-terminus—would be used.) Furthermore, use of the *E. coli* lac repressor N-terminus, e.g., which associates as a tetramer, with two coils facing in each direction could join two dimers (or polymers of dimers) end to end, either at their N- or C-termini depending upon which end the self-assembling peptides were placed. They could also join N- to C-termini. In any case, alone, they could only form a dimer, each end of which would be extensible by adding an appropriate chimer monomer (as shown for the simpler case in FIG. 9).

In an alternative embodiment, the self-assembling moiety can be fused to the N-termini of the chimer. In a specific embodiment, the self-assembling moiety is fused to at least a 10 amino acid portion of a T-even-like tail fiber protein.

A self assembling moiety that assembles into a heterolinkgomer can also be used. For example, if polymerization between beams is directed by the surface of a dimeric cross-β surface, addition of a heterodimeric unit with one surface which does not promote further polymerization would be very useful to cap the penultimate unit and thus terminate polymerization. If the two types of coiled regions of the self-assembling moiety are much more attractive to each other that to themselves, then all of the dimers will be heterodimers. Such is the case for the N-terminal Jun and Fos leucine zipper regions.

A further advantage to such heterodimeric units is the ability to stage polymerization and thus build one unit (or one surface in a 2D array) at a time. For example, suppose surface A attaches to B but neither attaches to itself ([A<->B] is used to symbolize this type of interaction). Mix A/A and B/B$_o$ (B$_o$ is attached to a matrix for easy purification). This will form B$_o$/B-A/A. Now wash out A/A and add B/B. The construct is now B$_o$/B-A/A-B/B. Now add A/A$_o$. The construct is now B$_o$/B-A/A-B/B-A/A$_o$ and no more beams can be added. There are of course many other possibilities.

APPLICATIONS

The uses of the nanostructures of the present invention are manifold and include applications that require highly regular, well-defined arrays of fibers, cages, or solids, which may include specific attachment sites that allow them to associate with other materials.

In one embodiment, a three-dimensional hexagonal array of tubes is used as a molecular sieve or filter, providing regular vertical pores of precise diameter for selective separation of particles by size. Such filters can be used for sterilization of solutions (i.e., to remove microorganisms or viruses), or as a series of molecular-weight cut-off filters. In this case, the protein components of the pores may be modified so as to provide specific surface properties (i.e., hydrophilicity or hydrophobicity, ability to bind specific ligands, etc.). Among the advantages of this type of filtration device is the uniformity and linearity of pores and the high pore to matrix ratio.

In another embodiment, long one-dimensional fibers are incorporated, for example, into paper or cement or plastic during manufacture to provide added wet and dry tensile strength.

In still another embodiment, different nanostructure arrays are impregnated into paper and fabric as anti-counterfeiting markers. In this case, a simple color-linked antibody reaction (such as those commercially available in kits) is used to verify the origin of the material. Alternatively, such nanostructure arrays could bind dyes or other substances, either before or after incorporation to color the paper or fabrics or modify their appearance or properties in other ways.

KITS

The invention also provides kits for making nanostructures, comprising in one or more containers the chimers and deletion constructs of the invention. For example, one such kit comprises in one or more containers purified gp35 and purified gp36-34 chimer. Another such kit comprises purified gp37-36 chimer.

The following examples are intended to illustrate the present invention without limiting its scope.

In the examples below, all restriction enzymes, nucleases, ligases, etc. are commercially available from numerous commercial sources, such as New England Biolabs (NEB), Beverly, Mass.; Life Technologies (GIBCO-BRL), Gaithersburg, Md.; and Boehringer Mannheim Corp. (BMC), Indianapolis, Ind.

EXAMPLE 1

DESIGN, CONSTRUCTION AND EXPRESSION OF INTERNALLY DELETED P37

The gene encoding gp37 contains two sites for the restriction enzyme Bgl II, the first cleavage occurring after nucleotide 293 and the second after nucleotide 1486 (the nucleotides are numbered from the initiator methionine codon ATG.) Thus, digestion of a DNA fragment encoding gp37 with BglII, excision of the intervening fragment (nucleotides 294–1485) and re-ligation of the 5' and 3' fragments results in the formation of an internally deleted gp37, designated ΔP37, in which arginine-98 is joined with serine-497.

The restriction digestion reaction mix contains:

| | |
|---|---|
| gp37 plasmid DNA (1 μg/μl) | 2 μl |
| NEB buffer #2 (10X) | 1 μl |
| H$_2$O | 6 μl |
| Bgl II (10 U/μl) | 1 μl |

The gp37 plasmid signifies a pT7-5 plasmid into which gene 37 has been inserted in the multiple cloning site, downstream of a good ribosome binding site and of gene 57 to chaperon the dimerization. The reaction is incubated for 1 h at 37° C. Then, 89 μl of T4 DNA ligase buffer and 1 μl of T4 DNA ligase are added, and the reaction is continued at 16° C. for 4 hours. 2 μl of the Stu I restriction enzyme are then added, and incubation continued at 37° C. for 1 h. (The Stu I restriction enzyme digests residual plasmids that were not cut by Bgl II in the first step, reducing their transformability by about 100-fold.)

The reaction mixture is then transformed into E. coli strain BL21, obtained from Novagen, using standard procedures. The transformation mixture is plated onto nutrient agar containing 100 μg/ml ampicillin, and the plates are incubated overnight at 37° C.

Colonies that appear after overnight incubation are picked, and plasmid DNA is extracted and digested with Bgl II as above. The restriction digests are resolved on 1% agarose gels. A successful deletion is evidenced by the appearance after gel electrophoresis of a new DNA fragment of 4.2 kbp, representing the undeleted part of gene 37 which is still attached to the plasmid and which re-formed a BglII site by ligation. The 1.2 kbp DNA fragment bounded by BglII sites in the original gene is no longer in the plasmid and so is missing from the gel.

Plasmids selected for the predicted deletion as above are transformed into E. coli strain BL21(DE3). Transformants are grown at 30° C. until the density (A$_{600}$) of the culture reaches 0.6. IPTG is then added to a final concentration of 0.4 mM and incubation is continued at 30° C. for 2 h, after which the cultures are chilled on ice. 20 μl of the culture is then removed and added to 20 μl of a two-fold concentrated "cracking buffer" containing 1% sodium dodecyl sulfate, glycerol, and tracking dye. 15 μl of this solution are loaded onto a 10% polyacrylamide gel; a second aliquot of 15 μl is first incubated in a boiling water bath for 3 min and then loaded on the same gel. After electrophoresis, the gel is fixed and stained. Expression of the deleted gp37 is evidenced by the appearance of a protein species migrating at an apparent molecular mass of 65–70,000 daltons in the boiled sample. The extent of dimerization is suggested by the intensity of higher-molecular mass species in the unboiled sample and/ or by the disappearance of the 65–70,000 dalton protein band.

The ability of the deleted polypeptide to dimerize appropriately is directly evaluated by testing its ability to be recognized by an anti-P37 antiserum that reacts only with mature P37 dimers, using a standard protein immunoblotting procedure.

An alternative assay for functional dimerization of the deleted P37 polypeptide (also referred to as ΔP37) is its ability to complement in vivo a T4 37⁻phage, by first inducing expression of the ΔP37 and then infecting with the T4 mutant, and detecting progeny phage.

A ΔP37 was prepared as described above, and found capable of complementing a T4 37⁻phage in vivo.

EXAMPLE 2

DESIGN, CONSTRUCTION AND EXPRESSION OF A gp37-36 CHIMER

The starting plasmid for this construction is one in which the gene encoding gp37 is cloned immediately upstream (i.e., 5') of the gene encoding gp36. The plasmid is digested with Hae III, which deletes the entire 3' region of gp37 DNA downstream of nucleotide 724 to the 3' terminus, and also removes the 5' end of gp36 DNA from the 5' terminus to nucleotide 349. The reaction mixture is identical to that described in Example 1, except that a different plasmid DNA is used, and the enzyme is HaeIII. Ligation using T4 DNA ligase, bacterial transformation, and restriction analysis are also performed as in Example 1. In this case, excision of the central portion of the gene 37-36 insert and religation reveals a novel insert of 346 in-frame codons, which is cut only once by HaeIII (after nucleotide 725). The resulting construct is then expressed in *E. coli* BL21(DE3) as described in Example 1.

Successful expression of the gp37-36 chimer is evidenced by the appearance of a protein product of about 35,000 daltons. This protein will have the first 242 N-terminal amino acids of gp37 fused to the final 104 C-terminal amino acids of gp36 (numbered 118–221.) The utility of this chimer depends upon its ability to dimerize and attach end-to-end. That is, carboxy termini of said polypeptide will have the capability of interacting with the amino terminus of the P37 protein dimer of bacteriophage T4 and to form an attached dimer, and the amino terminus of the dimer of said polypeptide will have the capability of interacting with other said chimer polypeptides. This property can be tested by assaying whether introduction of ΔP37 initiates dimerization and polymerization. Alternatively, polyclonal antibodies specific to P36 dimer may be used to detect P36 subsequent to initiation of dimerization by ΔP37.

A gp37-36 chimer was prepared similarly to the procedures described above, except that the restriction enzyme TaqI was used instead of HaeIII. Briefly, the 5' fragment resulting from TaqI digestion of gene 37 was ligated to the 3' fragment resulting from TaqI digestion of gene 36. This produced a construct encoding a gp37-36 chimer in which amino acids 1–48 of gp37 were fused to amino acids 100–221 of gp36. This construct was expressed in *E. coli* BL21(DE3), and the chimer was detected as an 18 kD protein. This gp37-36 chimer was found to inhibit the growth of wild type T4 when expression of the gp37-36 chimer was induced prior to infection (in an In vitro phage inhibition assay).

EXAMPLE 3

MUTATION OF THE GP37-36 CHIMER TO PRODUCE COMPLEMENTARY SUPPRESSORS

The goal of this construction is to produce two variants of a dimerizable P37-36 chimer: One in which the N-terminus of the polypeptide is mutated (A, designated *P37-36) and one in which the C-terminus of the polypeptide is mutated (B, designated P37-36*). The requirement is that the mutated *P37 N-terminus cannot form a joint with the wild-type P36 C-terminus, but only with the mutated *P36 N-terminus. The rationale is that A and B each cannot polymerize independently (as the parent P37-36 protein can), but can only associate with each other sequentially (i.e., P37-36*+*P37-36→P37-36*-*P37-36).

A second construct, *p37-P36*, is formed by recombining *P37-36 and P37-36* in vitro. When the monomers *gp37-36* and gp37-36 are mixed in the presence of P37 initiator, gp37-36 would dimerize and polymerize to (P37-36)n; similarly, *P37 would only catalyze the polymerization of *gp37-36* to (*P37-36*)n. In this case, the two chimers could be of different size and different primary sequence with different potential side-group interactions, and could initiate attachment at different surfaces depending on the attachment specificity of P37.

The starting bacterial strain is a su° strain of *E. coli* (which lacks the ability to suppress amber mutations). When this strain is infected with a mutant T4 bacteriophage containing amber mutations in genes 35, 36, and 37, phage replication is incomplete, since the tail fiber proteins cannot be synthesized. When this strain is first transformed with a plasmid that directs the expression of the wild type gp35, gp36 and gp37 genes and induced with IPTG, and subsequently infected with mutant phage, infectious phage particles are produced; this is evidenced by the appearance of "nibbled" colonies. Nibbled colonies do not appear round, with smooth edges, but rather have sectors missing. This is caused by attack of a microcolony by a single phage, which replicates and prevents the growth of the bacteria in the missing sector.

For the purposes of this construction, the 3'-terminal region of gene 36 (corresponding to the C-terminal region of gp36) is mutagenized with randomly doped oligonucleotides. Randomly doped oligonucleotides are prepared during chemical synthesis of oligonucleotides, by adding a trace amount (up to a few percent) of the other three nucleotides at a given position, so that the resulting oligonucleotide mix has a small percentage of incorrect nucleotides at that position. Incorporation of such oligonucleotides into the plasmid will result in random mutations (Hutchison et al., Methods.Enzymol. 202:356, 1991).

The mutagenized population of plasmids (containing, however, unmodified genes 36 and 37), is then transformed into the su° bacteria, followed by infection with the mutant T4 phage as above. In this case, the appearance of non-"nibbled" colonies indicates that the mutated gp36 C-termini can no longer interact with wild type P37 to form functional tail fibers. The putative gp36* phenotypes found in such non-nibbled colonies are checked for lack of dimeric N-termini by appropriate immunospecificity as outlined above, and positive colonies are used as source of plasmid for the next step.

Several of these mutated plasmids are recovered and subjected to a second round of mutagenesis, this time using doped oligonucleotides that introduce random mutations into the N-terminal region of gp37 present on the same plasmid. Again, the (now doubly) mutagenized plasmids are transformed into the supo strain of *E. coli* and transformants are infected with the mutant T4 phage. At this stage, bacterial plates are screened for the re-appearance of "nibbled" colonies. A nibbled colony at this stage indicates that the phage has replicated by virtue of suppression of the non-functional gp36* mutation(s) by the *P37 mutation. In other words, such colonies must contain novel *P37 polypeptides that have now acquired the ability to interact with the P36* proteins encoded on the same plasmid.

The *P37-36 and P37-36* paired suppressor chimers (A and B as above) are then constructed in the same manner as described in Example 2. In this case, however, *P37 is used in place of wild type P37 and P36* is used in place of wild type P36. A *P37-36* chimer can now be made by restriction of *P37-36 and P37-36* and religation in the recombined order. The *P37-36* can be mixed with the P37-36 chimer, and the polymerization of each can be accomplished independently in the presence of the other. This is useful when the rod-like central portion of these chimers have been modified in different ways.

EXAMPLE 4

DESIGN, CONSTRUCTION AND EXPRESSION OF A gp36-34 CHIMER

The starting plasmid for this construction is one in which the vector containing gene 57 and the gene encoding gp36 is cloned immediately upstream (i.e., 5') of the gene encoding gp34. The plasmid is digested with NdeI, which cuts after bp 219 of gene 36 and after bp 2594 of gene 34, thereby deleting the final 148 C-terminal codons from the pg36 moiety and the first 865 N-terminal codons from the gp34 moiety. The reaction mixture is identical to that described in Example 1, except that a different plasmid DNA is used, and the enzyme used is NdeI (NEB). Ligation using T4 DNA ligase, bacterial transformation, and restriction analysis are also performed as in Example 1. This results in a new hybrid gene encoding a protein of 497 amino acids (73 N-terminal amino acids of gp36 and 424 C-terminal amino acids of gp34, numbered 866–1289.)

As an alternative, the starting plasmid is cut with SphI at bp 648 in gene 34, and the Exo-Size Deletion Kit (NEB) is used to create deletions as described above.

The resulting construct is then expressed in *E. coli* BL21 (DE3) as described in Example 1. Successful expression of the gp36-34 chimer is evidenced by the appearance of a protein product of about 55,000 daltons. Preferably, the amino termini of the polypeptide homodimer have the capability of interacting with the gp35 protein, and then the carboxy termini have the capability of interacting with other attached gp35 molecules. Successful formation of the dimer can be detected by reaction with anti-P36 antibodies or by attachment of gp35 or by the in vitro phage inhibition assay described in Example 2.

EXAMPLE 5

ISOLATION OF THERMOLABILE PROTEINS FOR SELF-ASSEMBLY

Thermolabile structures can be utilized in nanostructures for: a) initiation of chimer polymerization (e.g., gp37-36) at low temperature and subsequent inactivation of and separation from the initiator at high temperature; b) initiation of angle formation between P36 and gp35 (e.g., variants of gp35 that have thermolabile attachment sites for P36 N-termini or P34 C-termini, a variant P36 that forms a thermolabile attachment to gp35, and a variant P34 with a thermolabile C-terminal attachment site.) Thermolability may be reversible, permitting reattachment of the appropriate termini when the lower temperature is restored, or it may be irreversible.

To create a variant gp37 that permits heat induced separation of the P36-P37 junction, the 5' end of gp37 DNA is randomly mutagenized using doped oligonucleotides as described above. The mutagenized DNA fragment is then recombined into T4 phage by infection of the cell containing the mutagenized DNA by a T4 phage containing two amber mutations flanking the mutagenized region. Following a low-multiplicity infection, non-amber phage are selected at low temperature on *E. coil* su° at 30° C. The progeny of these plaques are resuspended in buffered and challenged by heating at 60° C. At this temperature, wild-type tail fibers remain intact and functional, whereas the thermolabile versions release the terminal P37 units and thus render those phage non-infectious.

At this stage, wild type phage are removed by: 1) adsorbing the wild type phage to sensitive bacteria and sedimenting (or filtering out) the bacteria with the adsorbed wild type phage; or 2) reacting the lysate with anti-P37 antibody, followed by immobilized Protein A and removal of adsorbed wild type phage. Either method leaves the noninfectious mutant phage particles in the supernatant fluid or filtrate, from which they can be recovered. The non-infectious phage lacking terminal P37 moieties (and probably the rest of the tail fibers as well) are then urea treated with 6M urea, and mixed with bacterial spheroplasts to permit infection at low multiplicity whereupon they replicate at low temperature and release progeny. Alternatively, infectious phage are reconstituted by in vitro incubation of the mutant phage with wild type P37 at 30° C.; this is followed by infection of intact bacterial cells using the standard protocol. The latter method of infection specifically selects mutant phage in which the thermolability of the P36-P37 junction is reversible.

Using either method, the phage populations are subjected to multiple rounds of selection as above, after which individual phage particles are isolated by plaque purification at 30° C. Finally, the putative mutants are evaluated individually for the following characteristics: 1) loss of infectivity after incubation at high temperatures (40–60° C.), as measured by a decrease in titer; 2) loss of P37 after incubation at high temperature, as measured by decrease in binding of P37-specific antibody to phage particles; and 3) morphological changes in the tail fibers after incubation at high temperatures, as assessed by electron microscopy.

After mutants are isolated and their phenotypes confirmed, the P37 gene is sequenced. If the mutations localize to particular regions or residues, those sequences are targeted for site-directed mutagenesis to optimize the desired characteristics.

Finally, the mutant gene 37 is cloned into expression plasmids and expressed individually in *E. coli* as in Example 1. The mutant P37 dimers are then purified from bacterial extracts and used in vitro assembly reactions.

In a similar fashion, mutant gp35 polypeptides can be isolated that exhibit a thermolabile interaction with the N-terminus of P36 or the C-terminus of P34. For thermolabile interaction with P34, phage are incubated at high temperature, resulting in the loss of the entire distal half of the tail fiber (i.e., gp35-P36-P37). The only difference in the experimental protocol is that, in this case, 1) random mutagenesis is performed over the entire gp35 gene; 2) wild-type phage (and distal half-fibers from thermolabile mutants) are separated from thermolabile mutant phage that have been inactivated at high temperature (but still have proximal half tail fibers attached) by precipitating both the distal half-fibers and the phage particles containing intact tail fibers with any of the anti-distal half tail-fiber antibodies followed by Staphylococcal A-protein beads; 3) the mutant phage remaining in the supernatant are reactivated by incubation at low temperature with bacterial extracts containing wild type intact distal half fibers; and 4) stocks of thermolabile gene, 35 mutants grown at 30° C. can be tested for reversible thermolability by inactivation at 60° C. and reincubation at 30° C. Inactivation is performed on a concentrated suspension of phage, and reincubation at 30° C. is performed either before or after dilution. If phage are successfully reactivated before, but not after, dilution, this indicates that their gp35 is reversibly thermolabile.

To create a gene 36 mutation with a thermolabile gp35-P36 linkage, the C-terminus of gene 36 is mutagenized as described above, and the mutant selected for reversibility. An alternative is to mutagenize gp35 to create a gene 35 mutant in which the gp35-P36 linkage will dissociate at 60° C. In this case, incubation with anti-gp35 antibodies can be used to precipitate the phage without P36-P37 and thus to separate them from the wild-type phage and distal half-tail fibers (P36-P37), since the variant gp35 will remain attached to P34.

EXAMPLE 6

ASSEMBLY OF ONE-DIMENSIONAL RODS

A. Simple Assembly: The P37-36 chimer described in Example 2 is capable of self-assembly, but requires a P37 initiator to bind the first unit of the rod. Therefore, a P37 or a ΔP37 dimer is either attached to a solid matrix or is free in solution to serve as an initiator. If the initiator is, attached to a solid matrix, a thermolabile P37 dimer is preferably used. Addition of an extract containing gp37-36, or the purified gp37-36 chimer, results in the assembly of linear multimers of increasing length. In the matrix-bound case, the final rods are released by a brief incubation at high temperature (40–60° C., depending on the characteristics of the particular thermolabile P37 variant.)

The ratio of initiator to gp37-36 can be varied, and the size distribution of the rods is measured by any of the following methods: 1) Size exclusion chromatography; 2) Increase in the viscosity of the solution; and 3) Direct measurement by electron microscopy.

B. Staged assembly: The P37-36 variants *P37-36 and P37-36* described in Example 3 cannot self-polymerize. This allows the staged assembly of rods of defined length, according to the following protocol:

1. Attach initiator P37 (preferably thermolabile) to a matrix.

2. Add excess *gp37-36 to attach and oligomerize as P37-36 homooligomers to the N-terminus of P37.

3. Wash out unreacted *gp37-36 and flood with gp37-36*.

4. Wash out unreacted gp37-36* and flood with excess *gp37-36.

5. Repeat steps 2–4, n–1 times.

6. Release assembly from matrix by brief incubation at high temperature as above.

The linear dimensions of the protein rods in the batch will depend upon the lengths of the unit heterochimers and the number of cycles (n) of addition. This method has the advantage of insuring absolute reproducibility of rod length and a homogenous, monodisperse size distribution from one preparation to another.

EXAMPLE 7

STAGED ASSEMBLY OF POLYGONS

The following assembly strategy utilizes gp35 as an angle joint to allow the formation of polygons. For the purpose of this example, the angle formed by gp35 is assumed to be 137°. The rod unit comprises the P36-34 chimer described in Example 4, which is incapable of self-polymerization. The P36-34 homodimer is made from a bacterial clone in which both gp36-34 and gp57 are expressed. The gp57 can chaperone the homodimerization of gp36-34 to P36-34.

1. Initiator: The incomplete distal half fiber P36-37 is attached to a solid matrix by the P37 C-terminus. Thermolabile gp35 as described in Example 5 is then added to form the intact initiator.

2. Excess P36-34 chimer is added to attach a single P36-34. Following binding to the matrix via gp35, the unbound chimer is washed out.

3. Wild-type (i.e., non-thermolabile) gp35 is then added in excess. After incubation, the unbound material is washed out.

4. Steps 2 and 3 are repeated 7–8 times.

5. The assembly is released from the matrix by brief incubation at high temperature.

The released polymeric rod, 8 units long, will form a regular 8-sided polygon, whose sides comprise the P36-34 dimer and whose joints comprise the wild-type gp35 monomer. However, there will be some multimers of these 8 units bound as helices. When a unit does not close, but instead adds another to its terminus, the unit cannot close further and the helix can build in either direction. The direction of the first overlap also determines the handedness of the helix. Ten (or seven)-unit rods may form helices more frequently than polygons since their natural angles are 144° (or 128.6°). The likelihood of closure of a regular polygon depends not only on the average angle of gp35 but also on its flexibility, which can be further manipulated by genetic or environmental modification.

The type of polygon that is formed using this protocol depends upon the length of rod units and the angle formed by the angle joint. For example, alternating rod units of different sizes can be used in step 2. In addition, variant gp35 polypeptides that form angles different than the natural angle of 137° can be used, allowing the formation of different regular polygons. Furthermore, for a given polygon with an even number of sides and equal angles, the sides in either half can be of any size provided the two halves are symmetric.

What is claimed is:

1. An isolated DNA encoding a polypeptide consisting essentially of a fusion protein between the gp36 and gp37 proteins of bacteriophage T4, wherein amino acid residues 1–242 of gp37 (SEQ ID NO:6) are fused in proper reading frame amino terminal to amino acid residues 118–221 of gp36 (SEQ ID NO:5).

2. An isolated DNA encoding a polypeptide consisting essentially of a variant of the gp36 protein of bacteriophage T4, wherein said polypeptide lacks the capability of interacting with the amino terminus of the P37 protein oligomer of bacteriophage T4.

3. An isolated DNA encoding a polypeptide consisting essentially of a fusion protein between the gp36 and gp34 proteins of bacteriophage T4, wherein amino acid residues 1–73 of gp36 (SEQ ID NO:5) are fused in proper reading frame amino-terminal to amino acid residues 866–1289 of gp34 (SEQ ID NO:2).

4. An isolated DNA encoding a fusion protein consisting essentially of a first portion of a gp37 protein of a T-even-like bacteriophage consisting of in the range of the first 10–60 N-terminal amino acids of the gp37 protein fused to a second portion of a gp36 protein of a T-even-like bacteriophage consisting of in the range of the last 10–60 C-terminal amino acids of the gp36 protein.

5. An isolated DNA encoding a fusion protein consisting essentially of a first portion of a gp37 protein of a T-even-like bacteriophage consisting of at least the first 20 N-terminal amino acids of the gp37 protein fused to a second portion of a gp36 protein of a T-even-like bacteriophage consisting of at least the last 20 C-terminal amino acids of the gp36 protein.

6. An isolated DNA encoding a fusion protein consisting essentially of a first portion of a gp36 protein of a T-even-like bacteriophage consisting of at least the first 20 N-terminal amino acids of the gp36 protein fused to a second portion of a gp34 protein of a T-even-like bacteriophage consisting of at least the last 20 C-terminal amino acids of the gp34 protein.

7. An isolated DNA encoding a protein comprising at least 20 contiguous amino acids of the gp37, gp36, or gp34 protein of a T-even-like bacteriophage, and lacking at least 5 amino acids of the amino- or carboxy-terminus of the protein.

8. The isolated DNA of claim 7 encoding a protein comprising at least 20 contiguous amino acids of the gp37 protein of a T-even-like bacteriophage, and lacking at least 5 amino acids of the amino-terminus of the protein.

9. The isolated DNA of claim 7 encoding a protein comprising at least 20 contiguous amino acids of the gp36 protein of a T-even-like bacteriophage, and lacking at least 5 amino acids of the amino-terminus of the protein.

10. The isolated DNA of claim 7 encoding a protein comprising at least 20 contiguous amino acids of the gp36 protein of a T-even-like bacteriophage, and lacking at least 5 amino acids of the amino-terminus of the protein.

11. The isolated DNA of claim 7 encoding a protein comprising at least 20 contiguous amino acids of the gp37 protein of a T-even-like bacteriophage, and lacking at least 5 amino acids of the amino-terminus of the protein.

12. The isolated DNA of claim 7 encoding a protein comprising at least 20 contiguous amino acids of the gp37 protein of a T-even-like bacteriophage, and lacking at least 5 amino acids of the carboxy-terminus of the protein.

13. The isloated DNA of claim 7 encoding a protein comprising at least 20 contiguous amino acids of the gp34 protein of a T-even-like bacteriophage, and lacking at least 5 amino acids of the carboxy-terminus of the protein.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 8855 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacteriopha ge T4

(vii) IMMEDIATE SOURCE:
        (B) CLONE: TAIL FIBER GENES (xi) SEQUENCE DESCRIPTION: SEQ ID NO: 1:

| | | | | | |
|---|---|---|---|---|---|
| TAGGAGCCCG | GGAGAATGGC | CGAGATTAAA | AGAGAATTCA | GAGCAGAAGA T | GGTCTGGAC | 60 |
| GCAGGTGGTG | ATAAAATAAT | CAACGTAGCT | TTAGCTGATC | GTACCGTAGG A | ACTGACGGT | 120 |
| GTTAACGTTG | ATTACTTAAT | TCAAGAAAAC | ACAGTTCAAC | AGTATGATCC A | ACTCGTGGA | 180 |
| TATTTAAAAG | ATTTTGTAAT | CATTTATGAT | AACCGCTTTT | GGGCTGCTAT A | AATGATATT | 240 |
| CCAAAACCAG | CAGGAGCTTT | TAATAGCGGA | CGCTGGAGAG | CATTACGTAC C | GATGCTAAC | 300 |
| TGGATTACGG | TTTCATCTGG | TTCATATCAA | TTAAAATCTG | GTGAAGCAAT T | TCGGTTAAC | 360 |
| ACCGCAGCTG | GAAATGACAT | CACGTTTACT | TTACCATCTT | CTCCAATTGA T | GGTGATACT | 420 |
| ATCGTTCTCC | AAGATATTGG | AGGAAAACCT | GGAGTTAACC | AAGTTTTAAT T | GTAGCTCCA | 480 |
| GTACAAAGTA | TTGTAAACTT | TAGAGGTGAA | CAGGTACGTT | CAGTACTAAT G | ACTCATCCA | 540 |
| AAGTCACAGC | TAGTTTTAAT | TTTTAGTAAT | CGTCTGTGGC | AAATGTATGT T | GCTGATTAT | 600 |
| AGTAGAGAAG | CTATAGTTGT | AACACCAGCG | AATACTTATC | AAGCGCAATC C | AACGATTTT | 660 |
| ATCGTACGTA | GATTTACTTC | TGCTGCACCA | ATTAATGTCA | AACTTCCAAG A | TTTGCTAAT | 720 |
| CATGGCGATA | TTATTAATTT | CGTCGATTTA | GATAAACTAA | ATCCGCTTTA T | CATACAATT | 780 |
| GTTACTACAT | ACGATGAAAC | GACTTCAGTA | CAAGAAGTTG | GAACTCATTC C | ATTGAAGGC | 840 |
| CGTACATCGA | TTGACGGTTT | CTTGATGTTT | GATGATAATG | AGAAATTATG G | AGACTGTTT | 900 |
| GACGGGGATA | GTAAAGCGCG | TTTACGTATC | ATAACGACTA | ATTCAAACAT T | CGTCCAAAT | 960 |
| GAAGAAGTTA | TGGTATTTGG | TGCGAATAAC | GGAACAACTC | AAACAATTGA G | CTTAAGCTT | 1020 |
| CCAACTAATA | TTTCTGTTGG | TGATACTGTT | AAAATTTCCA | TGAATTACAT G | AGAAAAGGA | 1080 |
| CAAACAGTTA | AAATCAAAGC | TGCTGATGAA | GATAAAATTG | CTTCTTCAGT T | CAATTGCTG | 1140 |
| CAATTCCCAA | AACGCTCAGA | ATATCCACCT | GAAGCTGAAT | GGGTTACAGT T | CAAGAATTA | 1200 |
| GTTTTTAACG | ATGAAACTAA | TTATGTTCCA | GTTTTGGAGC | TTGCTTACAT A | GAAGATTCT | 1260 |
| GATGGAAAAT | ATTGGGTTGT | ACAGCAAAAC | GTTCCAACTG | TAGAAAGAGT A | GATTCTTTA | 1320 |
| AATGATTCTA | CTAGAGCAAG | ATTAGGCGTA | ATTGCTTTAG | CTACACAAGC T | CAAGCTAAT | 1380 |
| GTCGATTTAG | AAAATTCTCC | ACAAAAAGAA | TTAGCAATTA | CTCCAGAAAC G | TTAGCTAAT | 1440 |
| CGTACTGCTA | CAGAAACTCG | CAGAGGTATT | GCAAGAATAG | CAACTACTGC T | CAAGTGAAT | 1500 |
| CAGAACACCA | CATTCTCTTT | TGCTGATGAT | ATTATCATCA | CTCCTAAAAA G | CTGAATGAA | 1560 |
| AGAACTGCTA | CAGAAACTCG | TAGAGGTGTC | GCAGAAATTG | CTACGCAGCA A | GAAACTAAT | 1620 |
| GCAGGAACCG | ATGATACTAC | AATCATCACT | CCTAAAAAGC | TTCAAGCTCG T | CAAGGTTCT | 1680 |
| GAATCATTAT | CTGGTATTGT | AACCTTTGTA | TCTACTGCAG | GTGCTACTCC A | GCTTCTAGC | 1740 |

```
CGTGAATTAA ATGGTACGAA TGTTTATAAT AAAAACACTG ATAATTTAGT T GTTTCACCT   1800

AAAGCTTTGG ATCAGTATAA AGCTACTCCA ACACAGCAAG GTGCAGTAAT T TTAGCAGTT   1860

GAAAGTGAAG TAATTGCTGG ACAAAGTCAG CAAGGATGGG CAAATGCTGT T GTAACGCCA   1920

GAAACGTTAC ATAAAAAGAC ATCAACTGAT GGAAGAATTG GTTTAATTGA A ATTGCTACG   1980

CAAAGTGAAG TTAATACAGG AACTGATTAT ACTCGTGCAG TCACTCCTAA A ACTTTAAAT   2040

GACCGTAGAG CAACTGAAAG TTTAAGTGGT ATAGCTGAAA TTGCTACACA A GTTGAATTC   2100

GACGCAGGCG TCGACGATAC TCGTATCTCT ACACCATTAA AAATTAAAAC C AGATTTAAT   2160

AGTACTGATC GTACTTCTGT TGTTGCTCTA TCTGGATTAG TTGAATCAGG A ACTCTCTGG   2220

GACCATTATA CACTTAATAT TCTTGAAGCA ATGAGACAC AACGTGGTAC A CTTCGTGTA   2280

GCTACGCAGG TCGAAGCTGC TGCGGGAACA TTAGATAATG TTTTAATAAC T CCTAAAAAG   2340

CTTTTAGGTA CTAAATCTAC TGAAGCGCAA GAGGGTGTTA TTAAAGTTGC A ACTCAGTCT   2400

GAAACTGTGA CTGGAACGTC AGCAAATACT GCTGTATCTC CAAAAAATTT A AAATGGATT   2460

GCGCAGAGTG AACCTACTTG GCAGCTACT ACTGCAATAA GAGGTTTTGT T AAAACTTCA   2520

TCTGGTTCAA TTACATTCGT TGGTAATGAT ACAGTCGGTT CTACCCAAGA T TTAGAACTG   2580

TATGAGAAAA ATAGCTATGC GGTATCACCA TATGAATTAA ACCGTGTATT A GCAAATTAT   2640

TTGCCACTAA AAGCAAAAGC TGCTGATACA AATTTATTGG ATGGTCTAGA T TCATCTCAG   2700

TTCATTCGTA GGGATATTGC ACAGACGGTT AATGGTTCAC TAACCTTAAC C CAACAAACG   2760

AATCTGAGTG CCCCTCTTGT ATCATCTAGT ACTGGTGAAT TTGGTGGTTC A TTGGCCGCT   2820

AATAGAACAT TTACCATCCG TAATACAGGA GCCCCGACTA GTATCGTTTT C GAAAAAGGT   2880

CCTGCATCCG GGGCAAATCC TGCACAGTCA ATGAGTATTC GTGTATGGGG T AACCAATTT   2940

GGCGGCGGTA GTGATACGAC CCGTTCGACA GTGTTTGAAG TTGGCGATGA C ACATCTCAT   3000

CACTTTTATT CTCAACGTAA TAAAGACGGT AATATAGCGT TTAACATTAA T GGTACTGTA   3060

ATGCCAATAA ACATTAATGC TTCCGGTTTG ATGAATGTGA ATGGCACTGC A ACATTCGGT   3120

CGTTCAGTTA CAGCCAATGG TGAATTCATC AGCAAGTCTG CAAATGCTTT T AGAGCAATA   3180

AACGGTGATT ACGGATTCTT TATTCGTAAT GATGCCTCTA ATACCTATTT T TTGCTCACT   3240

GCAGCCGGTG ATCAGACTGG TGGTTTTAAT GGATTACGCC CATTATTAAT T AATAATCAA   3300

TCCGGTCAGA TTACAATTGG TGAAGGCTTA ATCATTGCCA AAGGTGTTAC T ATAAATTCA   3360

GGCGGTTTAA CTGTTAACTC GAGAATTCGT TCTCAGGGTA CTAAAACATC T GATTTATAT   3420

ACCCGTGCGC CAACATCTGA TACTGTAGGA TTCTGGTCAA TCGATATTAA T GATTCAGCC   3480

ACTTATAACC AGTTCCCGGG TTATTTTAAA ATGGTTGAAA AAACTAATGA A GTGACTGGG   3540

CTTCCATACT TAGAACGTGG CGAAGAAGTT AAATCTCCTG GTACACTGAC T CAGTTTGGT   3600

AACACACTTG ATTCGCTTTA CCAAGATTGG ATTACTTATC CAACGACGCC A GAAGCGCGT   3660

ACCACTCGCT GGACACGTAC ATGGCAGAAA ACCAAAAACT CTTGGTCAAG T TTTGTTCAG   3720

GTATTTGACG GAGGTAACCC TCCTCAACCA TCTGATATCG GTGCTTTACC A TCTGATAAT   3780

GCTACAATGG GGAATCTTAC TATTCGTGAT TTCTTGCGAA TTGGTAATGT T CGCATTGTT   3840

CCTGACCCAG TGAATAAAAC GGTTAAATTT GAATGGGTTG AATAAGAGGT A TTATGGAAA   3900

AATTTATGGC CGAGATTTGG ACAAGGATAT GTCCAAACGC CATTTTATCG G AAAGTAATT   3960

CAGTAAGATA TAAAATAAGT ATAGCGGGTT CTTGCCCGCT TTCTACAGCA G GACCATCAT   4020

ATGTTAAATT TCAGGATAAT CCTGTAGGAA GTCAAACATT TAGGCGCAGG C CTTCATTTA   4080

AGAGTTTTTG ACCCTTCCAC CGGAGCATTA GTTGATAGTA AGTCATATGC T TTTTCGACT   4140
```

-continued

```
TCAAATGATA CTACATCAGC TGCTTTTGTT AGTTTTCATG AATTCTTTGA C GAATAATCG    4200

AATTGTTGCT ATATTAACTA GTGGAAAGGT TAATTTTCCT CCTGAAGTAG T ATCTTGGTT    4260

AAGAACCGCC GGAACGTCTG CCTTTCCATC TGATTCTATA TTGTCAAGAT T TGACGTATC    4320

ATATGCTGCT TTTTATACTT CTTCTAAAAG AGCTATCGCA TTAGAGCATG T TAAACTGAG    4380

TAATAGAAAA AGCACAGATG ATTATCAAAC TATTTTAGAT GTTGTATTTG A CAGTTTAGA    4440

AGATGTAGGA GCTACCGGGT TTCCAAGAAG AACGTATGAA AGTGTTGAGC A ATTCATGTC    4500

GGCAGTTGGT GGAACTAATA ACGAAATTGC GAGATTGCCA ACTTCAGCTG C TATAAGTAA    4560

ATTATCTGAT TATAATTTAA TTCCTGGAGA TGTTCTTTAT CTTAAAGCTC A GTTATATGC    4620

TGATGCTGAT TTACTTGCTC TTGGAACTAC AAATATATCT ATCCGTTTTT A TAATGCATC    4680

TAACGGATAT ATTTCTTCAA CACAAGCTGA ATTTACTGGG CAAGCTGGGT C ATGGGAATT    4740

AAAGGAAGAT TATGTAGTTG TTCCAGAAAA CGCAGTAGGA TTTACGATAT A CGCACAGAG    4800

AACTGCACAA GCTGGCCAAG GTGGCATGAG AAATTTAAGC TTTTCTGAAG T ATCAAGAAA    4860

TGGCGGCATT TCGAAACCTG CTGAATTTGG CGTCAATGGT ATTCGTGTTA A TTATATCTG    4920

CGAATCCGCT TCACCTCCGG ATATAATGGT ACTTCCTACG CAAGCATCGT C TAAAACTGG    4980

TAAAGTGTTT GGGCAAGAAT TTAGAGAAGT TTAAATTGAG GGACCCTTCG G GTTCCCTTT    5040

TTCTTTATAA ATACTATTCA ATAAAGGGG CATACAATGG CTGATTTAAA A GTAGGTTCA    5100

ACAACTGGAG GCTCTGTCAT TTGGCATCAA GGAAATTTTC CATTGAATCC A GCCGGTGAC    5160

GATGTACTCT ATAAATCATT TAAAATATAT TCAGAATATA ACAAACCACA A GCTGCTGAT    5220

AACGATTTCG TTTCTAAAGC TAATGGTGGT ACTTATGCAT CAAAGGTAAC A TTTAACGCT    5280

GGCATTCAAG TCCCATATGC TCCAAACATC ATGAGCCCAT GCGGGATTTA T GGGGTAAC    5340

GGTGATGGTG CTACTTTTGA TAAAGCAAAT ATCGATATTG TTTCATGGTA T GGCGTAGGA    5400

TTTAAATCGT CATTTGGTTC AACAGGCCGA ACTGTTGTAA TTAATACACG C AATGGTGAT    5460

ATTAACACAA AAGGTGTTGT GTCGGCAGCT GGTCAAGTAA GAAGTGGTGC G GCTGCTCCT    5520

ATAGCAGCGA ATGACCTTAC TAGAAAGGAC TATGTTGATG GAGCAATAAA T ACTGTTACT    5580

GCAAATGCAA ACTCTAGGGT GCTACGGTCT GGTGACACCA TGACAGGTAA T TTAACAGCG    5640

CCAAACTTTT TCTCGCAGAA TCCTGCATCT CAACCCTCAC ACGTTCCACG A TTTGACCAA    5700

ATCGTAATTA AGGATTCTGT TCAAGATTTC GGCTATTATT AAGAGGACTT A TGGCTACTT    5760

TAAAACAAAT ACAATTTAAA AGAAGCAAAA TCGCAGGAAC ACGTCCTGCT G CTTCAGTAT    5820

TAGCCGAAGG TGAATTGGCT ATAAACTTAA AAGATAGAAC AATTTTTACT A AAGATGATT    5880

CAGGAAATAT CATCGATCTA GGTTTTGCTA AAGGCGGGCA AGTTGATGGC A ACGTTACTA    5940

TTAACGGACT TTTGAGATTA AATGGCGATT ATGTACAAAC AGGTGGAATG A CTGTAAACG    6000

GACCCATTGG TTCTACTGAT GGCGTCACTG GAAAAATTTT CAGATCTACA C AGGGTTCAT    6060

TTTATGCAAG AGCAACAAAC GATACTTCAA ATGCCCATTT ATGGTTTGAA A ATGCCGATG    6120

GCACTGAACG TGGCGTTATA TATGCTCGCC CTCAAACTAC AACTGACGGT G AAATACGCC    6180

TTAGGGTTAG ACAAGGAACA GGAAGCACTG CCAACAGTGA ATTCTATTTC C GCTCTATAA    6240

ATGGAGGCGA ATTTCAGGCT AACCGTATTT TAGCATCAGA TTCGTTAGTA A CAAAACGCA    6300

TTGCGGTTGA TACCGTTATT CATGATGCCA AAGCATTTGG ACAATATGAT T CTCACTCTT    6360

TGGTTAATTA TGTTTATCCT GGAACCGGTG AAACAAATGG TGTAAACTAT C TTCGTAAAG    6420

TTCGCGCTAA GTCCGGTGGT ACAATTTATC ATGAAATTGT TACTGCACAA A CAGGCCTGG    6480
```

```
CTGATGAAGT TTCTTGGTGG TCTGGTGATA CACCAGTATT TAAACTATAC G GTATTCGTG    6540

ACGATGGCAG AATGATTATC CGTAATAGCC TTGCATTAGG TACATTCACT A CAAATTTCC    6600

CGTCTAGTGA TTATGGCAAC GTCGGTGTAA TGGGCGATAA GTATCTTGTT C TCGGCGACA    6660

CTGTAACTGG CTTGTCATAC AAAAAAACTG GTGTATTTGA TCTAGTTGGC G GTGGATATT    6720

CTGTTGCTTC TATTACTCCT GACAGTTTCC GTAGTACTCG TAAAGGTATA T TTGGTCGTT    6780

CTGAGGACCA AGGCGCAACT TGGATAATGC CTGGTACAAA TGCTGCTCTC T TGTCTGTTC    6840

AAACACAAGC TGATAATAAC AATGCTGGAG ACGGACAAAC CCATATCGGG T ACAATGCTG    6900

GCGGTAAAAT GAACCACTAT TTCCGTGGTA CAGGTCAGAT GAATATCAAT A CCCAACAAG    6960

GTATGGAAAT TAACCCGGGT ATTTTGAAAT TGGTAACTGG CTCTAATAAT G TACAATTTT    7020

ACGCTGACGG AACTATTTCT TCCATTCAAC CTATTAAATT AGATAACGAG A TATTTTTAA    7080

CTAAATCTAA TAATACTGCG GGTCTTAAAT TTGGAGCTCC TAGCCAAGTT G ATGGCACAA    7140

GGACTATCCA ATGGAACGGT GGTACTCGCG AAGGACAGAA TAAAAACTAT G TGATTATTA    7200

AAGCATGGGG TAACTCATTT AATGCCACTG GTGATAGATC TCGCGAAACG G TTTTCCAAG    7260

TATCAGATAG TCAAGGATAT TATTTTTATG CTCATCGTAA AGCTCCAACC G GCGACGAAA    7320

CTATTGGACG TATTGAAGCT CAATTTGCTG GGGATGTTTA TGCTAAAGGT A TTATTGCCA    7380

ACGGAAATTT TAGAGTTGTT GGGTCAAGCG CTTTAGCCGG CAATGTTACT A TGTCTAACG    7440

GTTTGTTTGT CCAAGGTGGT TCTTCTATTA CTGGACAAGT TAAAATTGGC G GAACAGCAA    7500

ACGCACTGAG AATTTGGAAC GCTGAATATG GTGCTATTTT CCGTCGTTCG G AAAGTAACT    7560

TTTATATTAT TCCAACCAAT CAAAATGAAG GAGAAAGTGG AGACATTCAC A GCTCTTTGA    7620

GACCTGTGAG AATAGGATTA AACGATGGCA TGGTTGGGTT AGGAAGAGAT T CTTTTATAG    7680

TAGATCAAAA TAATGCTTTA ACTACGATAA ACAGTAACTC TCGCATTAAT G CCAACTTTA    7740

GAATGCAATT GGGGCAGTCG GCATACATTG ATGCAGAATG TACTGATGCT G TTCGCCCGG    7800

CGGGTGCAGG TTCATTTGCT TCCCAGAATA ATGAAGACGT CCGTGCGCCG T TCTATATGA    7860

ATATTGATAG AACTGATGCT AGTGCATATG TTCCTATTTT GAAACAACGT T ATGTTCAAG    7920

GCAATGGCTG CTATTCATTA GGGACTTTAA TTAATAATGG TAATTTCCGA G TTCATTACC    7980

ATGGCGGCGG AGATAACGGT TCTACAGGTC ACAGACTGC TGATTTTGGA T GGGAATTTA    8040

TTAAAAACGG TGATTTTATT TCACCTCGCG ATTTAATAGC AGGCAAAGTC A GATTTGATA    8100

GAACTGGTAA TATCACTGGT GGTTCTGGTA ATTTTGCTAA CTTAAACAGT A CAATTGAAT    8160

CACTTAAAAC TGATATCATG TCGAGTTACC CAATTGGTGC TCCGATTCCT T GGCCGAGTG    8220

ATTCAGTTCC TGCTGGATTT GCTTTGATGG AAGGTCAGAC CTTTGATAAG T CCGCATATC    8280

CAAAGTTAGC TGTTGCATAT CCTAGCGGTG TTATTCCAGA TATGCGCGGG C AAACTATCA    8340

AGGGTAAACC AAGTGGTCGT GCTGTTTTGA GCGCTGAGGC AGATGGTGTT A AGGCTCATA    8400

GCCATAGTGC ATCGGCTTCA AGTACTGACT TAGGTACTAA AACCACATCA A GCTTTGACT    8460

ATGGTACGAA GGGAACTAAC AGTACGGGTG GACACACTCA CTCTGGTAGT G GTTCTACTA    8520

GCACAAATGG TGAGCACAGC CACTACATCG AGGCATGGAA TGGTACTGGT G TAGGTGGTA    8580

ATAAGATGTC ATCATATGCC ATATCATACA GGGCGGGTGG GAGTAACACT A ATGCAGCAG    8640

GGAACCACAG TCACACTTTC TCTTTTGGGA CTAGCAGTGC TGGCGACCAT T CCCACTCTG    8700

TAGGTATTGG TGCTCATACC CACACGGTAG CAATTGGATC ACATGGTCAT A CTATCACTG    8760

TAAATAGTAC AGGTAATACA GAAAACACGG TTAAAAACAT TGCTTTTAAC T ATATCGTTC    8820

GTTTAGCATA AGGAGAGGGG CTTCGGCCCT TCTAA                                8855
```

(2) INFORMATION FOR SEQ ID NO: 2:

(i) SEQUENCE CHARACTERISTICS:
        (A) LENGTH: 1289 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p34 amino acid (xi) SEQUENCE DESCRIPTION: SEQ ID NO: 2:

```
Met Ala Glu Ile Lys Arg Glu Phe Arg Ala Glu Asp Gly Leu Asp Ala
 1               5                  10                  15

Gly Gly Asp Lys Ile Ile Asn Val Ala Leu Ala Asp Arg Thr Val Gly
                20                  25                  30

Thr Asp Gly Val Asn Val Asp Tyr Leu Ile Gln Glu Asn Thr Val Gln
            35                  40                  45

Gln Tyr Asp Pro Thr Arg Gly Tyr Leu Lys Asp Phe Val Ile Ile Tyr
    50                  55                  60

Asp Asn Arg Phe Trp Ala Ala Ile Asn Asp Ile Pro Lys Pro Ala Gly
65                  70                  75                  80

Ala Phe Asn Ser Gly Arg Trp Arg Ala Leu Arg Thr Asp Ala Asn Trp
                85                  90                  95

Ile Thr Val Ser Ser Gly Ser Tyr Gln Leu Lys Ser Gly Glu Ala Ile
            100                 105                 110

Ser Val Asn Thr Ala Ala Gly Asn Asp Ile Thr Phe Thr Leu Pro Ser
        115                 120                 125

Ser Pro Ile Asp Gly Asp Thr Ile Val Leu Gln Asp Ile Gly Gly Lys
    130                 135                 140

Pro Gly Val Asn Gln Val Leu Ile Val Ala Pro Val Gln Ser Ile Val
145                 150                 155                 160

Asn Phe Arg Gly Glu Gln Val Arg Ser Val Leu Met Thr His Pro Lys
                165                 170                 175

Ser Gln Leu Val Leu Ile Phe Ser Asn Arg Leu Trp Gln Met Tyr Val
            180                 185                 190

Ala Asp Tyr Ser Arg Glu Ala Ile Val Val Thr Pro Ala Asn Thr Tyr
        195                 200                 205

Gln Ala Gln Ser Asn Asp Phe Ile Val Arg Arg Phe Thr Ser Ala Ala
    210                 215                 220

Pro Ile Asn Val Lys Leu Pro Arg Phe Ala Asn His Gly Asp Ile Ile
225                 230                 235                 240

Asn Phe Val Asp Leu Asp Lys Leu Asn Pro Leu Tyr His Thr Ile Val
                245                 250                 255

Thr Thr Tyr Asp Glu Thr Thr Ser Val Gln Glu Val Gly Thr His Ser
            260                 265                 270

Ile Glu Gly Arg Thr Ser Ile Asp Gly Phe Leu Met Phe Asp Asp Asn
        275                 280                 285

Glu Lys Leu Trp Arg Leu Phe Asp Gly Asp Ser Lys Ala Arg Leu Arg
    290                 295                 300

Ile Ile Thr Thr Asn Ser Asn Ile Arg Pro Asn Glu Glu Val Met Val
305                 310                 315                 320
```

-continued

```
Phe Gly Ala Asn Asn Gly Thr Thr Gln Thr Ile Glu Leu Lys Leu Pro
                325                 330                 335

Thr Asn Ile Ser Val Gly Asp Thr Val Lys Ile Ser Met Asn Tyr Met
            340                 345                 350

Arg Lys Gly Gln Thr Val Lys Ile Lys Ala Ala Asp Glu Asp Lys Ile
        355                 360                 365

Ala Ser Ser Val Gln Leu Leu Gln Phe Pro Lys Arg Ser Glu Tyr Pro
    370                 375                 380

Pro Glu Ala Glu Trp Val Thr Val Gln Glu Leu Val Phe Asn Asp Glu
385                 390                 395                 400

Thr Asn Tyr Val Pro Val Leu Glu Leu Ala Tyr Ile Glu Asp Ser Asp
            405                 410                 415

Gly Lys Tyr Trp Val Val Gln Gln Asn Val Pro Thr Val Glu Arg Val
        420                 425                 430

Asp Ser Leu Asn Asp Ser Thr Arg Ala Arg Leu Gly Val Ile Ala Leu
    435                 440                 445

Ala Thr Gln Ala Gln Ala Asn Val Asp Leu Glu Asn Ser Pro Gln Lys
    450                 455                 460

Glu Leu Ala Ile Thr Pro Glu Thr Leu Ala Asn Arg Thr Ala Thr Glu
465                 470                 475                 480

Thr Arg Arg Gly Ile Ala Arg Ile Ala Thr Thr Ala Gln Val Asn Gln
            485                 490                 495

Asn Thr Thr Phe Ser Phe Ala Asp Asp Ile Ile Ile Thr Pro Lys Lys
        500                 505                 510

Leu Asn Glu Arg Thr Ala Thr Glu Thr Arg Arg Gly Val Ala Glu Ile
    515                 520                 525

Ala Thr Gln Gln Glu Thr Asn Ala Gly Thr Asp Asp Thr Thr Ile Ile
    530                 535                 540

Thr Pro Lys Lys Leu Gln Ala Arg Gln Gly Ser Glu Ser Leu Ser Gly
545                 550                 555                 560

Ile Val Thr Phe Val Ser Thr Ala Gly Ala Thr Pro Ala Ser Ser Arg
            565                 570                 575

Glu Leu Asn Gly Thr Asn Val Tyr Asn Lys Asn Thr Asp Asn Leu Val
        580                 585                 590

Val Ser Pro Lys Ala Leu Asp Gln Tyr Lys Ala Thr Pro Thr Gln Gln
    595                 600                 605

Gly Ala Val Ile Leu Ala Val Glu Ser Glu Val Ile Ala Gly Gln Ser
    610                 615                 620

Gln Gln Gly Trp Ala Asn Ala Val Val Thr Pro Glu Thr Leu His Lys
625                 630                 635                 640

Lys Thr Ser Thr Asp Gly Arg Ile Gly Leu Ile Glu Ile Ala Thr Gln
            645                 650                 655

Ser Glu Val Asn Thr Gly Thr Asp Tyr Thr Arg Ala Val Thr Pro Lys
        660                 665                 670

Thr Leu Asn Asp Arg Arg Ala Thr Glu Ser Leu Ser Gly Ile Ala Glu
    675                 680                 685

Ile Ala Thr Gln Val Glu Phe Asp Ala Gly Val Asp Asp Thr Arg Ile
    690                 695                 700

Ser Thr Pro Leu Lys Ile Lys Thr Arg Phe Asn Ser Thr Asp Arg Thr
705                 710                 715                 720

Ser Val Val Ala Leu Ser Gly Leu Val Glu Ser Gly Thr Leu Trp Asp
            725                 730                 735

His Tyr Thr Leu Asn Ile Leu Glu Ala Asn Glu Thr Gln Arg Gly Thr
```

-continued

```
                  740                 745                 750
Leu Arg Val Ala Thr Gln Val Glu Ala A la Gly Thr Leu Asp Asn
            755                 760                 765
Val Leu Ile Thr Pro Lys Lys Leu Leu Gly T hr Lys Ser Thr Glu Ala
770                 775                 780
Gln Glu Gly Val Ile Lys Val Ala Thr Gln S er Glu Thr Val Thr Gly
785                 790                 795                 800
Thr Ser Ala Asn Thr Ala Val Ser Pro Lys A sn Leu Lys Trp Ile Ala
            805                 810                 815
Gln Ser Glu Pro Thr Trp Ala Ala Thr A la Ile Arg Gly Phe Val
            820                 825                 830
Lys Thr Ser Ser Gly Ser Ile Thr Phe Val G ly Asn Asp Thr Val Gly
            835                 840                 845
Ser Thr Gln Asp Leu Glu Leu Tyr Glu Lys A sn Ser Tyr Ala Val Ser
            850                 855                 860
Pro Tyr Glu Leu Asn Arg Val Leu Ala Asn T yr Leu Pro Leu Lys Ala
865                 870                 875                 880
Lys Ala Ala Asp Thr Asn Leu Leu Asp Gly L eu Asp Ser Ser Gln Phe
            885                 890                 895
Ile Arg Arg Asp Ile Ala Gln Thr Val Asn G ly Ser Leu Thr Leu Thr
            900                 905                 910
Gln Gln Thr Asn Leu Ser Ala Pro Leu Val S er Ser Thr Gly Glu
            915                 920                 925
Phe Gly Gly Ser Leu Ala Ala Asn Arg Thr P he Thr Ile Arg Asn Thr
            930                 935                 940
Gly Ala Pro Thr Ser Ile Val Phe Glu Lys G ly Pro Ala Ser Gly Ala
945                 950                 955                 960
Asn Pro Ala Gln Ser Met Ser Ile Arg Val T rp Gly Asn Gln Phe Gly
            965                 970                 975
Gly Gly Ser Asp Thr Thr Arg Ser Thr Val P he Glu Val Gly Asp Asp
            980                 985                 990
Thr Ser His His Phe Tyr Ser Gln Arg Asn L ys Asp Gly Asn Ile Ala
            995                 1000                1005
Phe Asn Ile Asn Gly Thr Val Met Pro Ile A sn Ile Asn Ala Ser Gly
            1010                1015                1020
Leu Met Asn Val Asn Gly Thr Ala Thr Phe G ly Arg Ser Val Thr Ala
1025                1030                1035                1040
Asn Gly Glu Phe Ile Ser Lys Ser Ala Asn A la Phe Arg Ala Ile Asn
            1045                1050                1055
Gly Asp Tyr Gly Phe Phe Ile Arg Asn Asp A la Ser Asn Thr Tyr Phe
            1060                1065                1070
Leu Leu Thr Ala Ala Gly Asp Gln Thr Gly G ly Phe Asn Gly Leu Arg
            1075                1080                1085
Pro Leu Leu Ile Asn Asn Gln Ser Gly Gln I le Thr Ile Gly Glu Gly
            1090                1095                1100
Leu Ile Ile Ala Lys Gly Val Thr Ile Asn S er Gly Gly Leu Thr Val
1105                1110                1115                1120
Asn Ser Arg Ile Arg Ser Gln Gly Thr Lys T hr Ser Asp Leu Tyr Thr
            1125                1130                1135
Arg Ala Pro Thr Ser Asp Thr Val Gly Phe T rp Ser Ile Asp Ile Asn
            1140                1145                1150
Asp Ser Ala Thr Tyr Asn Gln Phe Pro Gly T yr Phe Lys Met Val Glu
            1155                1160                1165
```

```
Lys Thr Asn Glu Val Thr Gly Leu Pro Tyr L eu Arg Gly Glu Glu
    1170            1175            1180

Val Lys Ser Pro Gly Thr Leu Thr Gln Phe G ly Asn Thr Leu Asp Ser
1185            119 0           1195            1200

Leu Tyr Gln Asp Trp Ile Thr Tyr Pro Thr T hr Pro Glu Ala Arg Thr
        1205            1210            1215

Thr Arg Trp Thr Arg Thr Trp Gln Lys Thr L ys Asn Ser Trp Ser Ser
        1220            1225            1230

Phe Val Gln Val Phe Asp Gly Gly Asn Pro P ro Gln Pro Ser Asp Ile
        1235            1240            1245

Gly Ala Leu Pro Ser Asp Asn Ala Thr Met G ly Asn Leu Thr Ile Arg
        1250            1255            1260

Asp Phe Leu Arg Ile Gly Asn Val Arg Ile V al Pro Asp Pro Val Asn
1265            127 0           1275            1280

Lys Thr Val Lys Phe Glu Trp Val Glu
            1285

(2) INFORMATION FOR SEQ ID NO: 3:

(i) SEQUENCE CHARACTERISTICS:
        (A) LENGTH: 65 amino acids
        (B) TYPE: amino acid
        (D) TOPOLOGY: linear (ii) MOLECULE TYPE: protein (vi) ORIGINAL SOURCE:
        (A) ORGANISM: Bacteriopha ge T4

(vii) IMMEDIATE SOURCE:
        (B) CLONE: ORF X am ino acid (xi) SEQUENCE DESCRIPTION: SEQ ID NO: 3:

Met Glu Lys Phe Met Ala Glu Ile Trp Thr A rg Ile Cys Pro Asn Ala
1               5               10              15

Ile Leu Ser Glu Ser Asn Ser Val Arg Tyr L ys Ile Ser Ile Ala Gly
            20              25              30

Ser Cys Pro Leu Ser Thr Ala Gly Pro Ser T yr Val Lys Phe Gln Asp
        35              40              45

Asn Pro Val Gly Ser Gln Thr Phe Arg Arg A rg Pro Ser Phe Lys Ser
    50              55              60

Phe
65

(2) INFORMATION FOR SEQ ID NO: 4:

(i) SEQUENCE CHARACTERISTICS:
        (A) LENGTH: 295 amino acids
        (B) TYPE: amino acid
        (D) TOPOLOGY: linear (ii) MOLECULE TYPE: protein (vi) ORIGINAL SOURCE:
        (A) ORGANISM: Bacteriopha ge T4

(vii) IMMEDIATE SOURCE:
        (B) CLONE: p35 amino acid (xi) SEQUENCE DESCRIPTION: SEQ ID NO: 4:

Met Leu Phe Arg Leu Gln Met Ile Leu His G ln Leu Leu Leu Leu Val
1               5               10              15
```

```
Phe Met Asn Ser Leu Thr Asn Asn Arg Ile Val Ala Ile Leu Thr Ser
             20                  25                  30

Gly Lys Val Asn Phe Pro Pro Glu Val Val Ser Trp Leu Arg Thr Ala
             35                  40                  45

Gly Thr Ser Ala Phe Pro Ser Asp Ser Ile Leu Ser Arg Phe Asp Val
             50                  55                  60

Ser Tyr Ala Ala Phe Tyr Thr Ser Ser Lys Arg Ala Ile Ala Leu Glu
 65                  70                  75                  80

His Val Lys Leu Ser Asn Arg Lys Ser Thr Asp Asp Tyr Gln Thr Ile
                 85                  90                  95

Leu Asp Val Val Phe Asp Ser Leu Glu Asp Val Gly Ala Thr Gly Phe
             100                 105                 110

Pro Arg Arg Thr Tyr Glu Ser Val Glu Gln Phe Met Ser Ala Val Gly
             115                 120                 125

Gly Thr Asn Asn Glu Ile Ala Arg Leu Pro Thr Ser Ala Ala Ile Ser
         130                 135                 140

Lys Leu Ser Asp Tyr Asn Leu Ile Pro Gly Asp Val Leu Tyr Leu Lys
145                 150                 155                 160

Ala Gln Leu Tyr Ala Asp Ala Asp Leu Leu Ala Leu Gly Thr Thr Asn
                 165                 170                 175

Ile Ser Ile Arg Phe Tyr Asn Ala Ser Asn Gly Tyr Ile Ser Ser Thr
             180                 185                 190

Gln Ala Glu Phe Thr Gly Gln Ala Gly Ser Trp Glu Leu Lys Glu Asp
             195                 200                 205

Tyr Val Val Pro Glu Asn Ala Val Gly Phe Thr Ile Tyr Ala Gln
             210                 215                 220

Arg Thr Ala Gln Ala Gly Gln Gly Met Arg Asn Leu Ser Phe Ser
225                 230                 235                 240

Glu Val Ser Arg Asn Gly Gly Ile Ser Lys Pro Ala Glu Phe Gly Val
             245                 250                 255

Asn Gly Ile Arg Val Asn Tyr Ile Cys Glu Ser Ala Ser Pro Pro Asp
             260                 265                 270

Ile Met Val Leu Pro Thr Gln Ala Ser Ser Lys Thr Gly Lys Val Phe
         275                 280                 285

Gly Gln Glu Phe Arg Glu Val
         290                 295
```

(2) INFORMATION FOR SEQ ID NO: 5:

(i) SEQUENCE CHARACTERISTICS:
        (A) LENGTH: 221 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p36 amino acid (xi) SEQUENCE DESCRIPTION: SEQ ID NO: 5:

```
Met Ala Asp Leu Lys Val Gly Ser Thr Thr Gly Gly Ser Val Ile Trp
 1               5                  10                  15

His Gln Gly Asn Phe Pro Leu Asn Pro Ala Gly Asp Asp Val Leu Tyr
                 20                  25                  30

Lys Ser Phe Lys Ile Tyr Ser Glu Tyr Asn Lys Pro Gln Ala Ala Asp
```

```
                       35                  40                  45
Asn Asp Phe Val Ser Lys Ala Asn Gly Gly Thr Tyr Ala Ser Lys Val
    50                  55                  60
Thr Phe Asn Ala Gly Ile Gln Val Pro Tyr Ala Pro Asn Ile Met Ser
65                  70                  75                  80
Pro Cys Gly Ile Tyr Gly Gly Asn Gly Asp Gly Ala Thr Phe Asp Lys
                    85                  90                  95
Ala Asn Ile Asp Ile Val Ser Trp Tyr Gly Val Gly Phe Lys Ser Ser
                100                 105                 110
Phe Gly Ser Thr Gly Arg Thr Val Val Ile Asn Thr Arg Asn Gly Asp
                115                 120                 125
Ile Asn Thr Lys Gly Val Val Ser Ala Ala Gly Gln Val Arg Ser Gly
    130                 135                 140
Ala Ala Ala Pro Ile Ala Ala Asn Asp Leu Thr Arg Lys Asp Tyr Val
145                 150                 155                 160
Asp Gly Ala Ile Asn Thr Val Thr Ala Asn Ala Asn Ser Arg Val Leu
                    165                 170                 175
Arg Ser Gly Asp Thr Met Thr Gly Asn Leu Thr Ala Pro Asn Phe Phe
                180                 185                 190
Ser Gln Asn Pro Ala Ser Gln Pro Ser His Val Pro Arg Phe Asp Gln
                195                 200                 205
Ile Val Ile Lys Asp Ser Val Gln Asp Phe Gly Tyr Tyr
    210                 215                 220

(2) INFORMATION FOR SEQ ID NO: 6:

(i) SEQUENCE CHARACTERISTICS:
        (A) LENGTH: 1026 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p37 amino acid (xi) SEQUENCE DESCRIPTION: SEQ ID NO: 6:

Met Ala Thr Leu Lys Gln Ile Gln Phe Lys Arg Ser Lys Ile Ala Gly
1                   5                  10                  15
Thr Arg Pro Ala Ala Ser Val Leu Ala Glu Gly Glu Leu Ala Ile Asn
                    20                  25                  30
Leu Lys Asp Arg Thr Ile Phe Thr Lys Asp Ser Gly Asn Ile Ile
                35                  40                  45
Asp Leu Gly Phe Ala Lys Gly Gly Gln Val Asp Gly Asn Val Thr Ile
    50                  55                  60
Asn Gly Leu Leu Arg Leu Asn Gly Asp Tyr Val Gln Thr Gly Gly Met
65                  70                  75                  80
Thr Val Asn Gly Pro Ile Gly Ser Thr Asp Gly Val Thr Gly Lys Ile
                    85                  90                  95
Phe Arg Ser Thr Gln Gly Ser Phe Tyr Ala Arg Ala Thr Asn Asp Thr
                100                 105                 110
Ser Asn Ala His Leu Trp Phe Glu Asn Ala Asp Gly Thr Glu Arg Gly
                115                 120                 125
Val Ile Tyr Ala Arg Pro Gln Thr Thr Thr Asp Gly Glu Ile Arg Leu
    130                 135                 140
```

-continued

```
Arg Val Arg Gln Gly Thr Gly Ser Thr Ala Asn Ser Glu Phe Tyr Phe
145                 150                 155                 160

Arg Ser Ile Asn Gly Gly Glu Phe Gln Ala Asn Arg Ile Leu Ala Ser
            165                 170                 175

Asp Ser Leu Val Thr Lys Arg Ile Ala Val Asp Thr Val Ile His Asp
            180                 185                 190

Ala Lys Ala Phe Gly Gln Tyr Asp Ser His Ser Leu Val Asn Tyr Val
            195                 200                 205

Tyr Pro Gly Thr Gly Glu Thr Asn Gly Val Asn Tyr Leu Arg Lys Val
    210                 215                 220

Arg Ala Lys Ser Gly Gly Thr Ile Tyr His Glu Ile Val Thr Ala Gln
225                 230                 235                 240

Thr Gly Leu Ala Asp Glu Val Ser Trp Trp Ser Gly Asp Thr Pro Val
                245                 250                 255

Phe Lys Leu Tyr Gly Ile Arg Asp Asp Gly Arg Met Ile Ile Arg Asn
                260                 265                 270

Ser Leu Ala Leu Gly Thr Phe Thr Thr Asn Phe Pro Ser Ser Asp Tyr
                275                 280                 285

Gly Asn Val Gly Val Met Gly Asp Lys Tyr Leu Val Leu Gly Asp Thr
290                 295                 300

Val Thr Gly Leu Ser Tyr Lys Lys Thr Gly Val Phe Asp Leu Val Gly
305                 310                 315                 320

Gly Gly Tyr Ser Val Ala Ser Ile Thr Pro Asp Ser Phe Arg Ser Thr
                325                 330                 335

Arg Lys Gly Ile Phe Gly Arg Ser Glu Asp Gln Gly Ala Thr Trp Ile
                340                 345                 350

Met Pro Gly Thr Asn Ala Ala Leu Leu Ser Val Gln Thr Gln Ala Asp
                355                 360                 365

Asn Asn Asn Ala Gly Asp Gly Gln Thr His Ile Gly Tyr Asn Ala Gly
                370                 375                 380

Gly Lys Met Asn His Tyr Phe Arg Gly Thr Gly Gln Met Asn Ile Asn
385                 390                 395                 400

Thr Gln Gln Gly Met Glu Ile Asn Pro Gly Ile Leu Lys Leu Val Thr
                405                 410                 415

Gly Ser Asn Asn Val Gln Phe Tyr Ala Asp Gly Thr Ile Ser Ser Ile
                420                 425                 430

Gln Pro Ile Lys Leu Asp Asn Glu Ile Phe Leu Thr Lys Ser Asn Asn
                435                 440                 445

Thr Ala Gly Leu Lys Phe Gly Ala Pro Ser Gln Val Asp Gly Thr Arg
450                 455                 460

Thr Ile Gln Trp Asn Gly Gly Thr Arg Glu Gly Gln Asn Lys Asn Tyr
465                 470                 475                 480

Val Ile Ile Lys Ala Trp Gly Asn Ser Phe Asn Ala Thr Gly Asp Arg
                485                 490                 495

Ser Arg Glu Thr Val Phe Gln Val Ser Asp Ser Gln Gly Tyr Tyr Phe
                500                 505                 510

Tyr Ala His Arg Lys Ala Pro Thr Gly Asp Glu Thr Ile Gly Arg Ile
                515                 520                 525

Glu Ala Gln Phe Ala Gly Asp Val Tyr Ala Lys Gly Ile Ile Ala Asn
                530                 535                 540

Gly Asn Phe Arg Val Val Gly Ser Ser Ala Leu Ala Gly Asn Val Thr
545                 550                 555                 560
```

-continued

```
Met Ser Asn Gly Leu Phe Val Gln Gly Gly Ser Ser Ile Thr Gly Gln
                565                 570                 575

Val Lys Ile Gly Gly Thr Ala Asn Ala Leu Arg Ile Trp Asn Ala Glu
            580                 585                 590

Tyr Gly Ala Ile Phe Arg Arg Ser Glu Ser Asn Phe Tyr Ile Ile Pro
            595                 600                 605

Thr Asn Gln Asn Glu Gly Glu Ser Gly Asp Ile His Ser Ser Leu Arg
        610                 615                 620

Pro Val Arg Ile Gly Leu Asn Asp Gly Met Val Gly Leu Gly Arg Asp
625                 630                 635                 640

Ser Phe Ile Val Asp Gln Asn Asn Ala Leu Thr Thr Ile Asn Ser Asn
                645                 650                 655

Ser Arg Ile Asn Ala Asn Phe Arg Met Gln Leu Gly Gln Ser Ala Tyr
            660                 665                 670

Ile Asp Ala Glu Cys Thr Asp Ala Val Arg Pro Ala Gly Ala Gly Ser
            675                 680                 685

Phe Ala Ser Gln Asn Asn Glu Asp Val Arg Ala Pro Phe Tyr Met Asn
        690                 695                 700

Ile Asp Arg Thr Asp Ala Ser Ala Tyr Val Pro Ile Leu Lys Gln Arg
705                 710                 715                 720

Tyr Val Gln Gly Asn Gly Cys Tyr Ser Leu Gly Thr Leu Ile Asn Asn
                725                 730                 735

Gly Asn Phe Arg Val His Tyr His Gly Gly Gly Asp Asn Gly Ser Thr
            740                 745                 750

Gly Pro Gln Thr Ala Asp Phe Gly Trp Glu Phe Ile Lys Asn Gly Asp
            755                 760                 765

Phe Ile Ser Pro Arg Asp Leu Ile Ala Gly Lys Val Arg Phe Asp Arg
        770                 775                 780

Thr Gly Asn Ile Thr Gly Gly Ser Gly Asn Phe Ala Asn Leu Asn Ser
785                 790                 795                 800

Thr Ile Glu Ser Leu Lys Thr Asp Ile Met Ser Ser Tyr Pro Ile Gly
                805                 810                 815

Ala Pro Ile Pro Trp Pro Ser Asp Ser Val Pro Ala Gly Phe Ala Leu
            820                 825                 830

Met Glu Gly Gln Thr Phe Asp Lys Ser Ala Tyr Pro Lys Leu Ala Val
            835                 840                 845

Ala Tyr Pro Ser Gly Val Ile Pro Asp Met Arg Gly Gln Thr Ile Lys
850                 855                 860

Gly Lys Pro Ser Gly Arg Ala Val Leu Ser Ala Glu Ala Asp Gly Val
865                 870                 875                 880

Lys Ala His Ser His Ser Ala Ser Ala Ser Ser Thr Asp Leu Gly Thr
                885                 890                 895

Lys Thr Thr Ser Ser Phe Asp Tyr Gly Thr Lys Gly Thr Asn Ser Thr
            900                 905                 910

Gly Gly His Thr His Ser Gly Ser Gly Ser Thr Ser Thr Asn Gly Glu
            915                 920                 925

His Ser His Tyr Ile Glu Ala Trp Asn Gly Thr Gly Val Gly Gly Asn
        930                 935                 940

Lys Met Ser Ser Tyr Ala Ile Ser Tyr Arg Ala Gly Gly Ser Asn Thr
945                 950                 955                 960

Asn Ala Ala Gly Asn His Ser His Thr Phe Ser Phe Gly Thr Ser Ser
                965                 970                 975

Ala Gly Asp His Ser His Ser Val Gly Ile Gly Ala His Thr His Thr
```

```
                  980            985            990
Val Ala Ile Gly Ser His Gly His Thr Ile T hr Val Asn Ser Thr Gly
            995            1000           1005
Asn Thr Glu Asn Thr Val Lys Asn Ile Ala P he Asn Tyr Ile Val Arg
       1010           1015           1020
Leu Ala
1025
```